(12) United States Patent
Fruland et al.

(10) Patent No.: US 9,636,139 B2
(45) Date of Patent: May 2, 2017

(54) TISSUE-REMOVING CATHETER WITH BALL AND SOCKET DEPLOYMENT MECHANISM

(71) Applicant: Covidien LP, Mansfield, MA (US)

(72) Inventors: Benjamin Fruland, Blaine, MN (US); John Pedersen, Eden Prairie, MN (US); Scott Petersen, Mansfield, MA (US); Robert Van Pelt, Saint Paul, MN (US); Thomas McPeak, Shakopee, MN (US)

(73) Assignee: Covidien LP, Mansfield, MA (US)

( * ) Notice: Subject to any disclaimer, the term of this patent is extended or adjusted under 35 U.S.C. 154(b) by 536 days.

(21) Appl. No.: 14/102,131

(22) Filed: Dec. 10, 2013

(65) Prior Publication Data

US 2014/0222049 A1  Aug. 7, 2014

Related U.S. Application Data

(60) Provisional application No. 61/736,198, filed on Dec. 12, 2012.

(51) Int. Cl.
*A61B 17/3207* (2006.01)
*A61B 17/22* (2006.01)
*A61B 17/00* (2006.01)

(52) U.S. Cl.
CPC .............. *A61B 17/320783* (2013.01); *A61B 17/320758* (2013.01); *A61B 2017/00685* (2013.01); *A61B 2017/320775* (2013.01); *A61B 2017/320791* (2013.01)

(58) Field of Classification Search
CPC .......... A61B 17/3205; A61B 17/32053; A61B 17/3207; A61B 17/320708; A61B 17/320725; A61B 17/32075; A61B 17/320758; A61B 17/320783; A61B 17/320016; A61B 17/32002; A61B 2017/320716; A61B 2017/320733; A61B 2017/320741; A61B 2017/320766; A61B 2017/320775; A61B 2017/320791; A61B 2017/320004; A61B 2017/320024; A61B 2017/320028; A61B 17/320032; A61B 17/00008; A61B 2017/32002
USPC ........................................................ 606/159
See application file for complete search history.

(56) References Cited

U.S. PATENT DOCUMENTS

| | | |
|---|---|---|
| 4,290,427 A | 9/1981 | Chin |
| 4,631,052 A | 12/1986 | Kensey |
| 4,765,332 A | 8/1988 | Fischell et al. |
| 4,790,813 A | 12/1988 | Kensey |
| 4,926,858 A | 5/1990 | Gifford, III et al. |
| 4,950,277 A | 8/1990 | Farr |
| 5,026,383 A | 6/1991 | Nobles |

(Continued)

*Primary Examiner* — Darwin Erezo
*Assistant Examiner* — Katherine Schwiker

(57) ABSTRACT

A deployment mechanism of a tissue-removing catheter includes a socket member received in a catheter body that is capable of moving longitudinally therein, and a ball member extending distally from the distal end portion of the cutting element and operatively connected to the socket member. The ball member is constrained axially relative to the socket member and is capable of pivoting relative to the socket member for allowing pivoting of the cutting element relative to the socket when the cutting element is moved from a retracted position to a cutting position.

19 Claims, 25 Drawing Sheets

(56) References Cited

U.S. PATENT DOCUMENTS

| | | | |
|---|---|---|---|
| 5,053,044 A * | 10/1991 | Mueller | A61B 17/320725 604/96.01 |
| 5,085,662 A | 2/1992 | Willard | |
| 5,100,424 A | 3/1992 | Jang et al. | |
| 5,123,904 A | 6/1992 | Shimomura et al. | |
| 5,176,693 A | 1/1993 | Pannek, Jr. | |
| 5,192,291 A | 3/1993 | Pannek, Jr. | |
| 5,226,909 A | 7/1993 | Evans et al. | |
| 5,242,460 A | 9/1993 | Klein et al. | |
| 5,350,390 A | 9/1994 | Sher | |
| 5,507,760 A | 4/1996 | Wynne et al. | |
| 5,507,795 A | 4/1996 | Chiang et al. | |
| 5,556,408 A | 9/1996 | Farhat | |
| 5,569,277 A | 10/1996 | Evans et al. | |
| 5,601,580 A | 2/1997 | Goldberg et al. | |
| 5,620,456 A | 4/1997 | Sauer et al. | |
| 5,776,156 A | 7/1998 | Shikhman | |
| 5,857,982 A | 1/1999 | Milliman et al. | |
| 6,053,923 A | 4/2000 | Veca et al. | |
| 6,068,603 A | 5/2000 | Suziki | |
| 6,110,127 A | 8/2000 | Suziki | |
| 6,126,667 A * | 10/2000 | Barry | A61B 17/320758 606/159 |
| 6,355,005 B1 * | 3/2002 | Powell | A61M 25/09 600/434 |
| 6,428,539 B1 | 8/2002 | Baxter et al. | |
| 6,503,263 B2 | 1/2003 | Adams | |
| RE38,018 E | 3/2003 | Anctil et al. | |
| 6,579,298 B1 | 6/2003 | Bruneau et al. | |
| RE38,335 E | 11/2003 | Aust et al. | |
| 6,652,549 B1 * | 11/2003 | Welten | A61B 17/00008 606/159 |
| 7,329,267 B2 | 2/2008 | Weber | |
| 7,344,546 B2 | 3/2008 | Wulfmann et al. | |
| 7,485,125 B2 | 2/2009 | Sjostrom | |
| 7,520,886 B2 | 4/2009 | Surti | |
| 7,635,340 B2 | 12/2009 | Vetter et al. | |
| 7,699,790 B2 | 4/2010 | Simpson | |
| 7,862,518 B2 | 1/2011 | Parihar | |
| 7,918,803 B2 | 4/2011 | Ritchart et al. | |
| 7,927,784 B2 | 4/2011 | Simpson | |
| 7,951,161 B2 | 5/2011 | Bonnette et al. | |
| 7,981,128 B2 | 7/2011 | To et al. | |
| 8,012,164 B1 | 9/2011 | Donohoe et al. | |
| 8,052,704 B2 | 11/2011 | Olson | |
| 8,062,316 B2 | 11/2011 | Patel et al. | |
| 8,070,762 B2 | 12/2011 | Escudero et al. | |
| 2002/0022788 A1 * | 2/2002 | Corvi | A61B 10/0275 600/564 |
| 2004/0006358 A1 | 1/2004 | Wulfman et al. | |
| 2006/0095043 A1 * | 5/2006 | Martz | A61B 17/1671 606/90 |
| 2007/0055259 A1 | 3/2007 | Norton et al. | |
| 2007/0276419 A1 | 11/2007 | Rosenthal | |
| 2007/0282358 A1 | 12/2007 | Remiszewski et al. | |
| 2008/0045986 A1 | 2/2008 | To et al. | |
| 2008/0065124 A1 | 3/2008 | Olson | |
| 2008/0140104 A1 | 6/2008 | Bender et al. | |
| 2009/0023988 A1 * | 1/2009 | Korner | A61B 17/1624 600/106 |
| 2009/0254092 A1 * | 10/2009 | Albiol Llorach | A61B 17/32 606/87 |
| 2010/0198240 A1 | 8/2010 | Simpson et al. | |
| 2011/0004107 A1 | 1/2011 | Rosenthal et al. | |
| 2011/0087258 A1 | 4/2011 | Sluss | |
| 2011/0130777 A1 | 6/2011 | Zhang et al. | |
| 2011/0144673 A1 | 6/2011 | Zhang et al. | |
| 2011/0152906 A1 | 6/2011 | Escudero et al. | |
| 2011/0190801 A1 | 8/2011 | Mark et al. | |
| 2011/0282242 A1 * | 11/2011 | Cronin | A61B 10/0275 600/567 |
| 2011/0301626 A1 | 12/2011 | To et al. | |
| 2011/0306995 A1 | 12/2011 | Moberg | |

* cited by examiner

TISSUE-REMOVING CATHETER WITH BALL AND SOCKET DEPLOYMENT MECHANISM

CROSS-REFERENCE TO RELATED APPLICATIONS

The present application claims priority to U.S. Provisional Application Ser. No. 61/736,198, filed Dec. 12, 2012, the entirety of which is hereby incorporated by reference in its entirety.

FIELD OF THE DISCLOSURE

The present invention generally relates to a tissue-removing catheter with a ball and socket deployment mechanism.

BACKGROUND

Vascular disease frequently arises from the accumulation of atheromatous material on the inner walls of vascular lumens, particularly arterial lumens of the peripheral and other vasculature, especially peripheral arteries, resulting in a condition known as atherosclerosis. Atherosclerosis occurs naturally as a result of aging, but may also be aggravated by factors such as diet, hypertension, heredity, vascular injury, and the like. Atheromatous deposits can have widely varying properties, with some deposits being relatively soft and others being fibrous and/or calcified. In the latter case, the deposits are frequently referred to as plaque.

Vascular disease can be treated in a variety of ways, including drugs, bypass surgery, and a variety of catheter-based approaches, including those which rely on intravascular tissue-removing or removal of the atheromatous or other material occluding a blood vessel. A variety of methods for cutting or dislodging material and removing such material from the blood vessel have been proposed, generally being referred to as atherectomy procedures. Atherectomy catheters intended to cut or excise material from the blood vessel lumen may employ a rotatable cutting blade (or other tissue-removing element) which can be advanced into or past the occlusive material in order to cut and separate such material from the blood vessel lumen.

It is desirous to provide catheters which can access small, tortuous regions of body lumens and which can remove tissue and/or other occluding materials from within body lumens in a controlled fashion. In one instance, it may be desired to provide atherectomy catheters which can facilitate capturing atheromatous materials. The catheters and methods for use in a variety of body lumens, including but not limited to coronary, peripheral, and other arteries, and other body lumens.

SUMMARY

A deployment mechanism of a tissue-removing catheter includes a socket member received in a catheter body that is capable of moving longitudinally therein, and a ball member extending distally from the distal end portion of the cutting element and operatively connected to the socket member. The ball member is constrained axially relative to the socket member and is capable of pivoting relative to the socket member for allowing pivoting of the cutting element relative to the socket when the cutting element is moved from a retracted position to a cutting position.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the distal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal portion of the catheter body. In other cases, it may be possible to provide a fixed or integral coil tip or guidewire tip on the distal portion of the catheter or even dispense with the guidewire entirely. For convenience of illustration, guidewires will not be shown in the illustrated embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, including both coronary arteries and peripheral arteries, by conventional techniques.

Figure 1A:
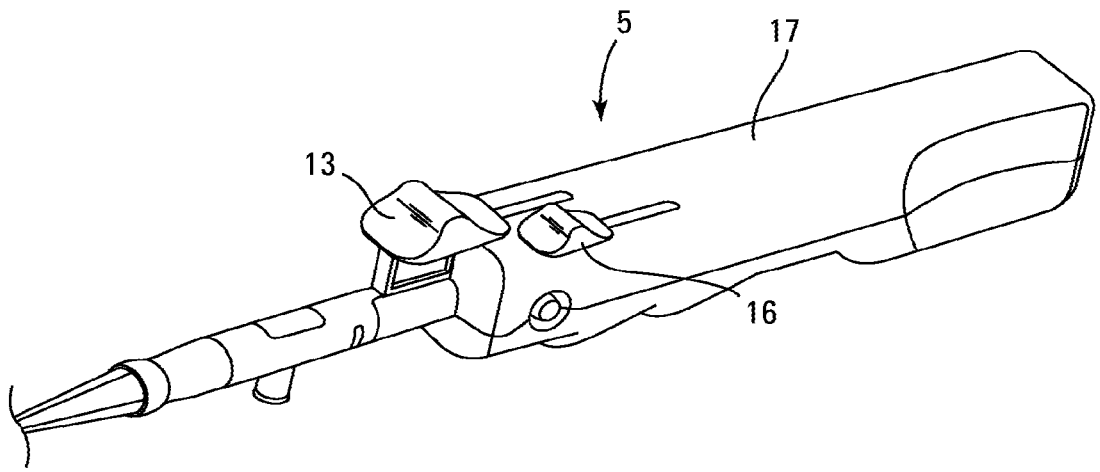
FIG. 1A is a perspective of a cutting element driver for an atherectomy catheter.

Referring to FIG. 1A an atherectomy catheter 2 is shown. Catheter 2 has a cutting element 4, which is used to cut material from a blood flow lumen such as an arterial or venous blood vessel. Catheter 2 may include an abrasive rotating tip 7, which is used to bore through any occlusion in a lumen that may otherwise prevent distal movement of the catheter through the vessel and is discussed in greater detail below. It should be noted that the abrasive tip is optional and the atherectomy catheter may be manufactured with no abrasive tip depending upon the application. The cutting element is mounted at the distal end of a flexible drive shaft 20. Drive shaft 20 extends through a lumen 21 in catheter 2. Catheter 2 includes a tissue collection chamber 12. In some embodiments tissue collection chamber 12 is a slotted metallic tube with a covering of polymer such as heat shrink tubing. In other embodiments tissue collection chamber 12 is a length of catheter body 8 located proximal to window 6. Catheter body 8 may be provided with a sidewall opening with tubing attached thereto (neither shown) to facilitate suction of cut debris or injection of fluid (including medications) through the annular space between catheter body and drive shaft 20. Catheter 2 is coupled to at its proximal end to a handle such as exemplary cutting element driver 5.

Figure 1B:
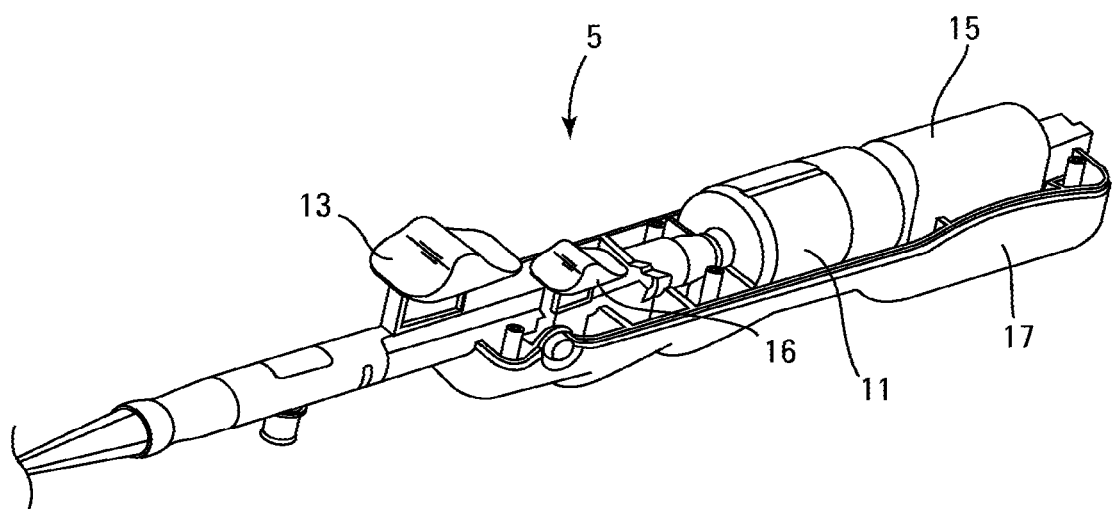
FIG. 1B is similar to FIG. 1A with a top housing portion of the cutting element driver removed.
Figure 3:
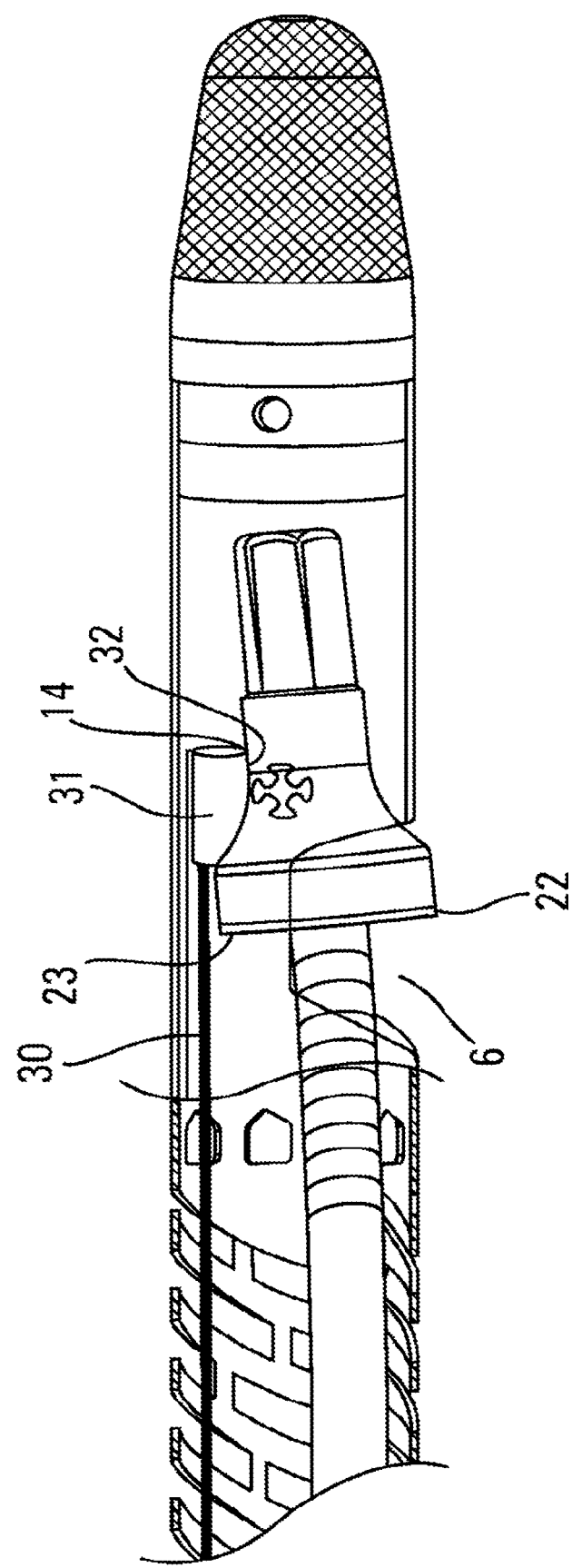
FIG. 3 is similar to FIG. 2B, with the cutting element in a cutting position.

Cutting element driver 5 is comprised of motor 11, power source 15 (for example, one or more batteries), microswitch (not shown), housing 17 (upper half of housing is removed as shown in FIG. 1B), lever 13, lever 16 and connection assembly (not shown) for connecting shaft 20 to driver motor 11. Cutting element driver 5 can act as a handle for the user to manipulate catheter 2. Lever 13 moves between a forward, or distal position, and a rearward, or proximal position. Lever 13 is operatively coupled to drive shaft 20 so that advancement or retraction of lever 13 causes corresponding advancement or retraction of drive shaft 20, which in turn controls the position of the cutting element in the housing, as shown in FIG. 3. As will be discussed in more detail hereafter, when lever 13 is in the forward position cutting element 4 is in its retracted position and when lever 13 is in the rearward position cutting element 4 is in its cutting position. Although not shown, cutting element driver 5 includes a switch to electrically connect power source 15 to motor 11 thereby causing rotation of cutting element 4. Lever 16 moves between a forward, or distal position, and a rearward, or proximal position. Lever 16 is operatively coupled to a pull wire 30. Pull wire 30 is attached to a bushing 31. As will be discussed in more detail hereafter, lever 16 is in the forward position when the cutting element is in the retracted position. When cutting element 4 is moved to its cutting position lever 16 is moved to the rearward position to cause the cutting element to extend through the cutting window. The cutting element 4 is rotated about a longitudinal axis LA when the shaft 20 rotates. The cutting element 4 is rotated about 1 to 160,000 rpm but may be rotated at any other suitable speed depending upon the particular application.

The cutting element 4 may be formed of one continuous part or may be comprised of multiple parts subsequently joined together by welding, soldering, brazing, adhesive bonding, mechanical interlock or other means. The cutting element includes a cutting element drive adaptor 41, which is adapted to receive and connect to the drive shaft, and a cutting edge 22, which is at a radially outer edge 23 of the cutting element 4. The drive shaft may be connected to the cutting element drive adaptor by welding, soldering, brazing, or adhesive bonding. Alternatively, the connection may be by mechanical interlock, or other means.

Figure 5:
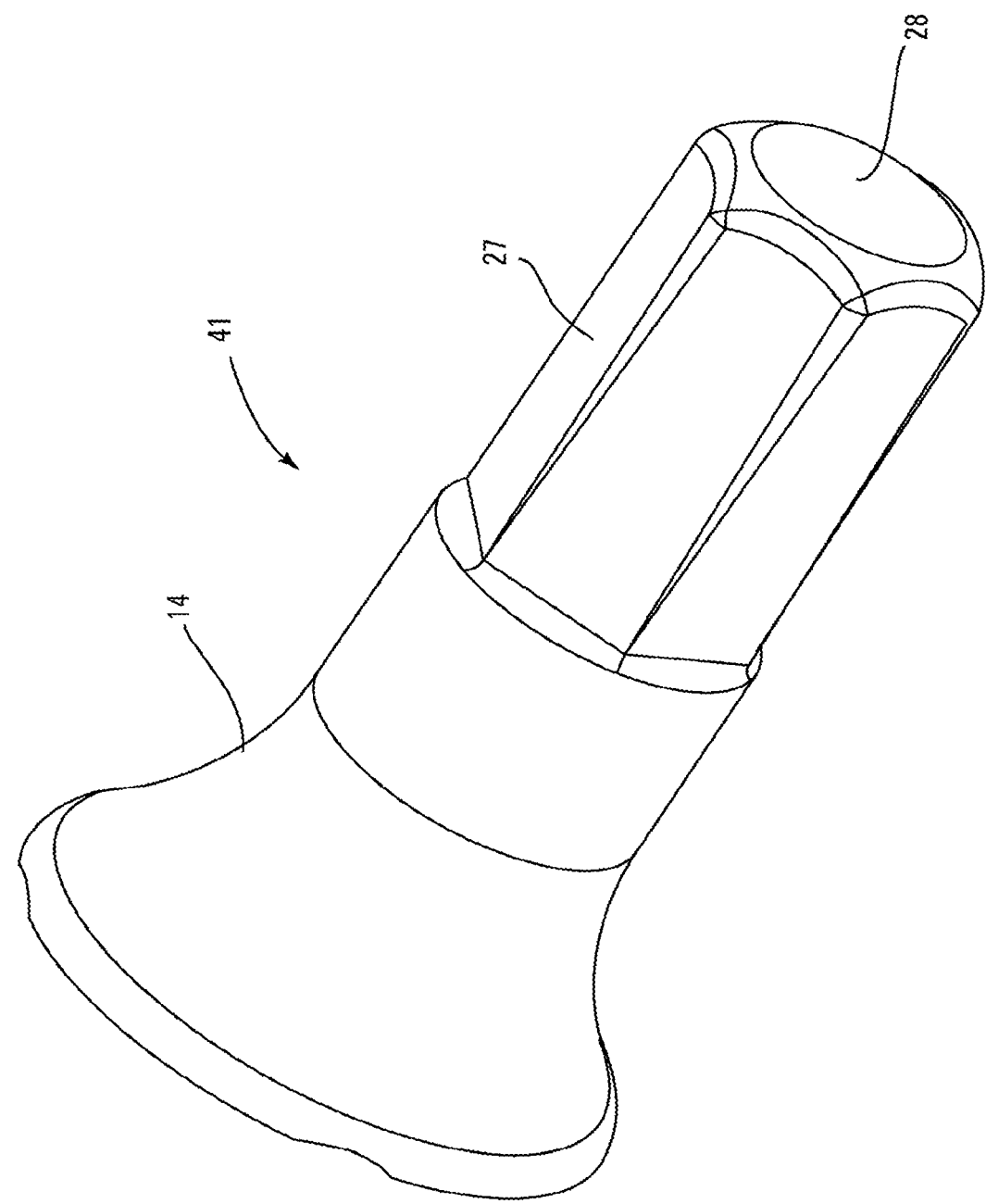
FIG. 5 is an enlarged perspective of a cutting element drive adaptor.

In FIG. 5 the cutting element drive adaptor is shown separated from the rest of the cutting element. In this embodiment drive shaft 20 may be hollow, having a lumen which forms a guidewire lumen. The cutting element drive adaptor has an opening configured to receive the distal end portion of the drive shaft. The cutting element drive adaptor may include a lumen 28 positioned to align with the guidewire lumen of the drive shaft to allow a guidewire to pass through the cutting element drive adaptor.

Figure 4A:
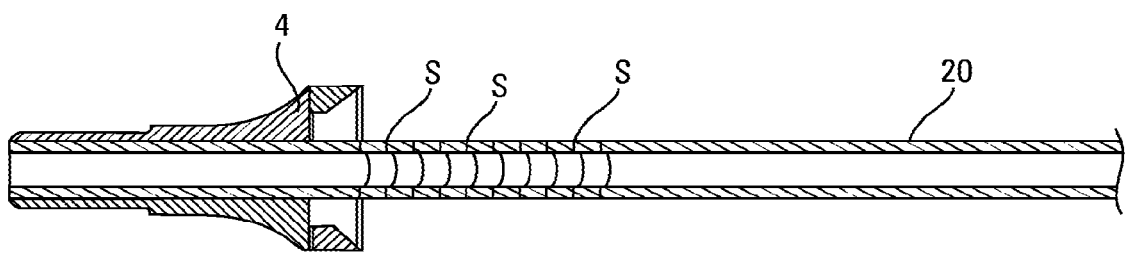
FIG. 4A is a longitudinal section of a cutting element and a fragmentary portion of a drive shaft of the catheter of FIG. 2A.
Figure 4B:
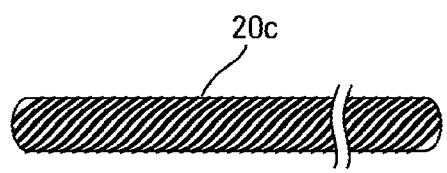
FIG. 4B is a fragmentary side view of an embodiment of the drive shaft for the catheter of FIG. 2A.

The drive shaft may be made from any suitable material having sufficient flexibility. For example, the drive shaft may comprise braided wires, helically wound wires or a solid tube. In one embodiment as shown in FIG. 4B, drive shaft 20c is made of helically wound stainless steel wires that may be left hand or right hand wound and that have welded proximal and distal ends that do not extend past the outside dimension of the braided steel wires. In some embodiments drive shaft 20c is comprised of multiple layers of helically wound wires, in some cases adjacent layers of helical wound wires are wound with opposite handedness.

The guidewire lumen extends from the proximal end to the distal end of drive shaft 20 so that the catheter may be used as an over-the-wire catheter. In a rapid exchange embodiment of the catheter shown in FIG. 16 the catheter is provided with a shortened guidewire lumen. In the rapid exchange embodiment the drive shaft need not have a guidewire lumen and, therefore, may optionally be solid or at least need not be hollow.

By manipulating lever 13 the cutting element 4 is movable, by an operator, between a retracted position (FIG. 2B) and a cutting position (FIG. 3) relative to an opening or cutting window 6 in a body 8 of the catheter 2. In the retracted position the cutting element is positioned distal to the cutting window within an enclosed distal portion of the catheter. In moving from the retracted position to the cutting position the cutting element is moved proximally in a longitudinal or axial direction to a position within the cutting window by moving lever 13 (and drive shaft 20) proximally. As described in more detail hereafter, the cutting element 4 is thereafter moved outwardly relative to the opening 6 so that a portion of the cutting element 4 extends outwardly from the body 8 through the opening 6. More specifically, a portion of the cutting element moves radially outwardly to a position beyond an outer diameter of the catheter body at the location of the cutting window. In one embodiment the cutting element 4 may be positioned relative to the body 8 and opening 6 so that less than 90 degrees of the cutting element 4 is exposed to cut tissue. In other embodiments more or less of the cutting element 4 may be exposed without departing from numerous aspects of the invention.

During use of the catheter, the catheter is advanced through the vessel until opening 6 is positioned adjacent or just distal to the distal end of a treatment site of a vessel with cutting element 4 in the retracted position. The cutting element is then moved proximally from the retracted position to the cutting position. Once the cutting element has been moved to the proper longitudinal position within the catheter body it is tilted outwardly so that a portion of cutting edge 22 of the cutting element extends beyond a diameter of the catheter housing. The cutting element 4 has a general cylindrical or tubular shape. The cutting edge 22 extends circumferentially around a proximal end of the cutting element and is oriented in a generally proximal direction. Once the cutting element 4 has been thus extended, the catheter 2 is pulled proximally through the vessel with the cutting element 4 in the working or cutting position. As the catheter 2 moves through the blood vessel with the cutting element 4 in the working or cutting position the tissue material is cut by the cutting edge 22 of cutting element 4 and is directed into a tissue collection chamber 12 positioned proximal to the cutting element 4. The tissue collection chamber 12 may be somewhat elongated to accommodate the tissue which has been cut.

As mentioned previously, the catheter body 8 may be provided with a side wall opening at a proximal location which can be connected by tubing to a suction source so that debris created by the rotating cutting element 4 can be aspirated through the annular space between the catheter body and drive shaft 20. The tissue collection chamber may be as long as the catheter length which is proximal to the window. The proximal portion of the catheter body may additionally have a sidewall opening or port (not shown) so tissue transported through the catheter can exit through the sidewall port. However, since the tissue collection chamber is positioned proximal of the cutting window its length is not constrained by the location, size, or morphology of the treatment site. Therefore, the tissue collection chamber 12 can be made to have any desired length.

Cutting element 4 is exposed through opening 6 through the use of a cutting element blade exposure mechanism comprising a pull wire 30 attached to a bushing 31. As best seen in cross-section in FIG. 2B, bushing 31 has a curved or cam surface 32. When the treatment site has been reached, opening 6 is positioned just distally of the lesion to be treated. Lever 13 is then moved proximally to its rearward position to move the drive shaft and cutting element proximally to a position within the cutting window. To expose the cutting element through the cutting window, lever 16 is moved proximally to its rearward position so that pull wire 30 is withdrawn proximally by the operator while the catheter body and cutting element 4 are maintained in a stationary position. As the pull wire 30 is withdrawn, cam surface 32 of bushing 31 acts against an angular ramp surface 14 of cutting element drive adaptor 41, causing the cutting element to tilt outwardly so that the cutting edge 22 of the cutting element extends beyond the outer surface of the catheter housing and through opening 6, as shown in FIG. 3. The distance by which cam surface 32 is moved in the proximal direction with respect to ramp surface 14 of the cutting element drive adapter 41 determines the distance that the cutting edge extends beyond the outer surface of the catheter. If pull wire 30 is withdrawn a further distance proximally, cam surface 32 of bushing 31 will move further proximally and act on the ramp surface 14 of the cutting element drive adaptor 41 to cause it to tilt outwardly at a greater angle so that the cutting edge 22 extends a further distance through opening 6. The amount or distance that cutting edge 22 extends through opening 6 determines the cutting depth of the material removed from the lumen during the procedure. The cutting depth can be controlled by careful manipulation of lever 16 so that the atheroma can be removed from the treatment site at a preselected cut depth. To facilitate precise control of lever 16 it can be equipped with a ratchet and pawl mechanism (not shown), or can be threadably engaged with the handle, or otherwise configured to allow incremental movement and/or positional locking of bushing 31. Pull wire 30 may comprise a metallic wire or other suitable material and may have a substantially constant diameter. Alternatively, pull wire 30 may have a flattened or arcuate cross-section. Pull wire 30 may be contained in lumen 21 of catheter 2 or may be housed in a separate lumen (not shown) within catheter 2. Bushing 31 may have an arcuate cross-sectional shape extending within lumen 21 of catheter 2 for 180 degrees, or less so that it does not interfere with the extension of the cutting element through the opening.

Figure 17A:
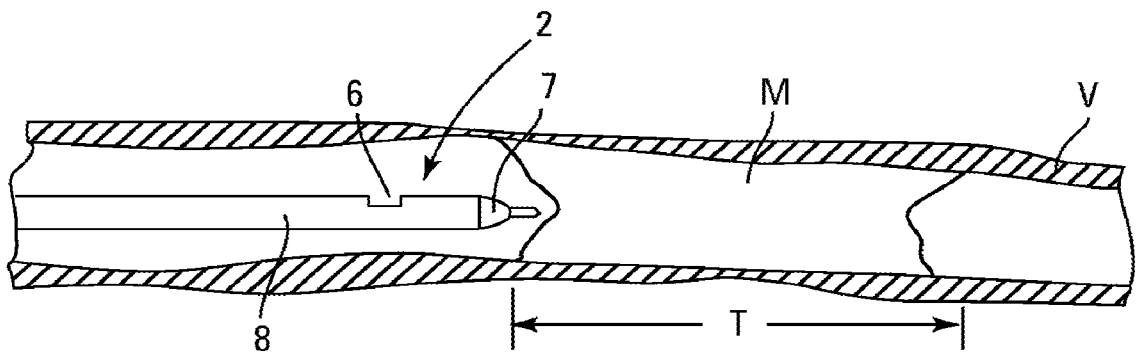
FIGS. 17A, 17B and 17C are fragmentary section of the catheter illustrating the method of using the atherectomy catheter.
Figure 17B:
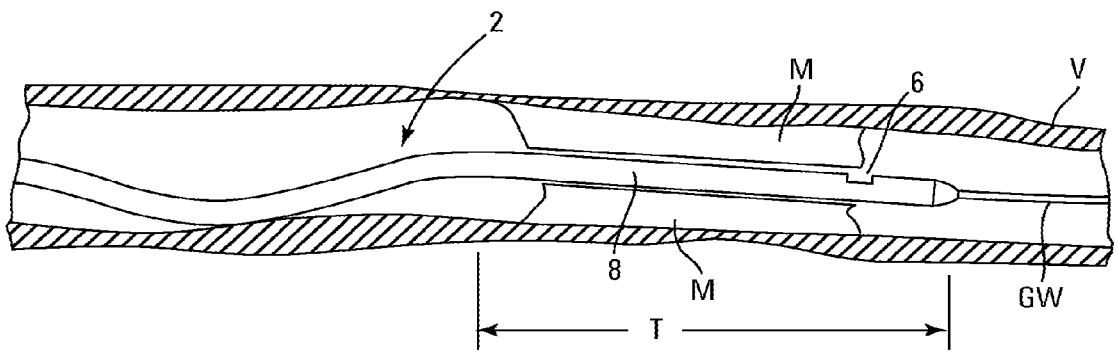
Figure 17C:
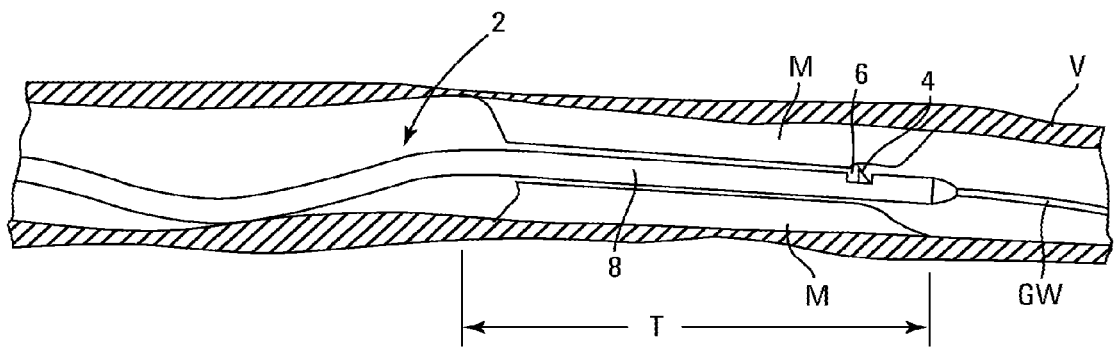

Once the cutting element 4 has been extended into opening 6, the drive motor is engaged to rotate the cutting element (through drive shaft 20) and catheter 2 is proximally withdrawn through the lumen of the vessel to remove material from the lesion. As best seen in FIGS. 17A to 17C, catheter 2 may also comprise a bend or curved shape towards the distal end which may help urge the cutting window 6 and cutting element 4 toward a wall of a body lumen to enhance treatment. Such a bend increases the working range of the catheter by allowing the cutting element to be urged against a lumen wall across a wider diameter lumen.

Figure 2A:
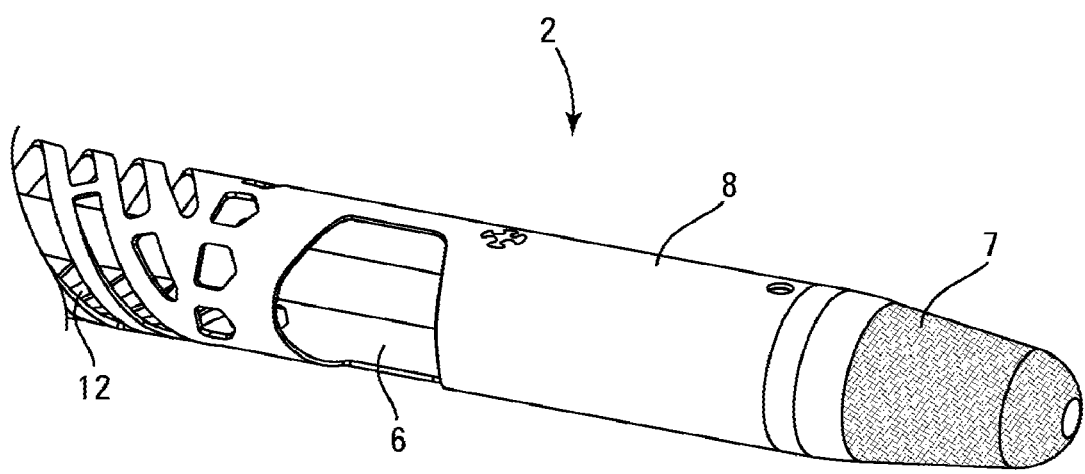
FIG. 2A is a fragmentary perspective view of a distal end portion of an atherectomy catheter.
Figure 2B:
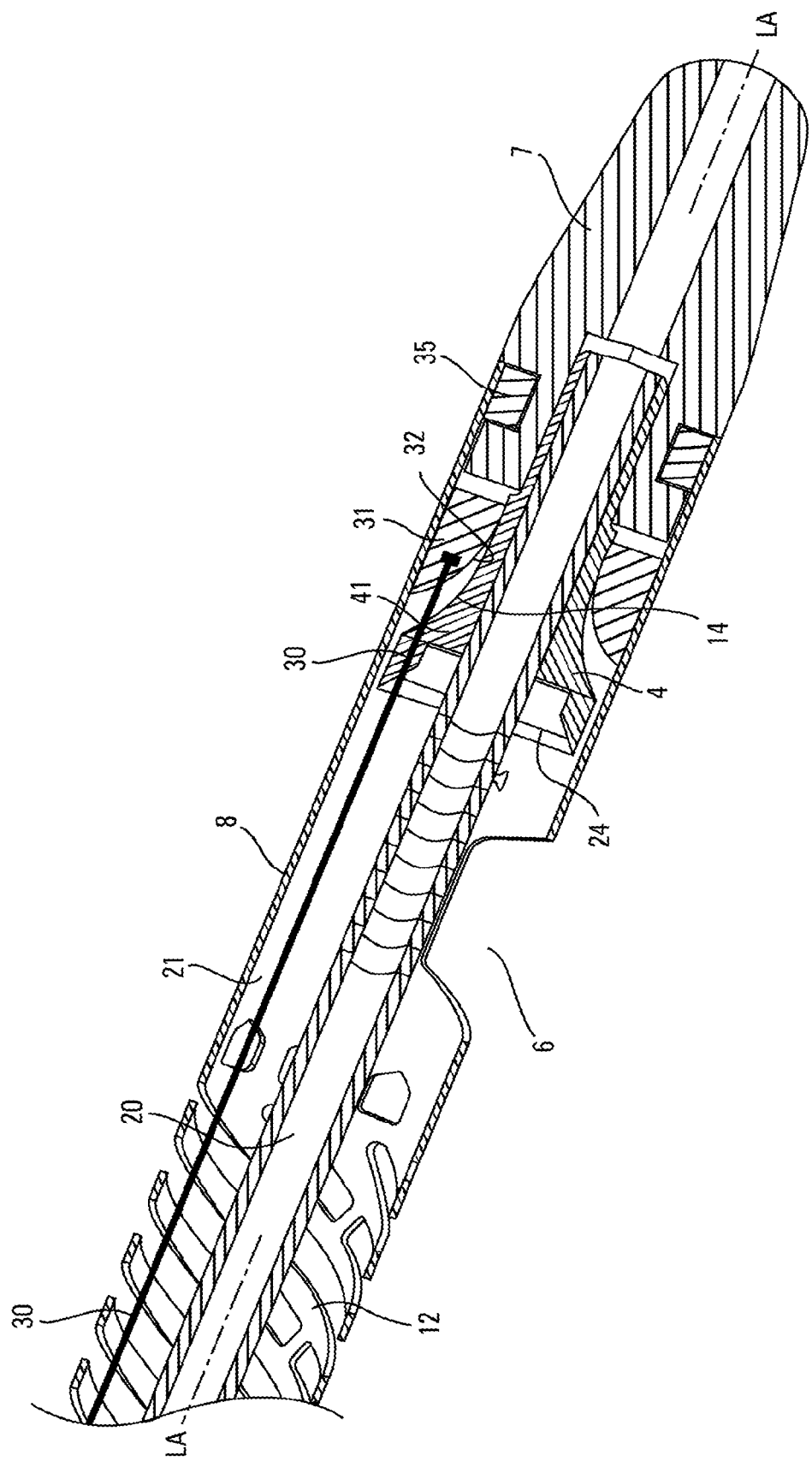
FIG. 2B is an enlarged longitudinal section of the distal end portion of FIG. 2A with a cutting element in a retracted position.

The cutting element 4 may have a cup-shaped surface 24, which directs the tissue cut by the cutting edge 22 into tissue chamber 12 (see FIG. 2B). Cutting edge 22 may be at a radially outer edge 23 of the cutting element 4. In some embodiments the cup-shaped surface 24 may be a smooth and continuous surface free of through holes, teeth, fins or other features, which disrupt the smooth nature of the surface 24 for at least half the distance from the longitudinal axis LA to the outer radius at the cutting edge 22. In other embodiments the cup shaped surface may have a limited amount of through holes, teeth, fins or other features.

Figure 6:
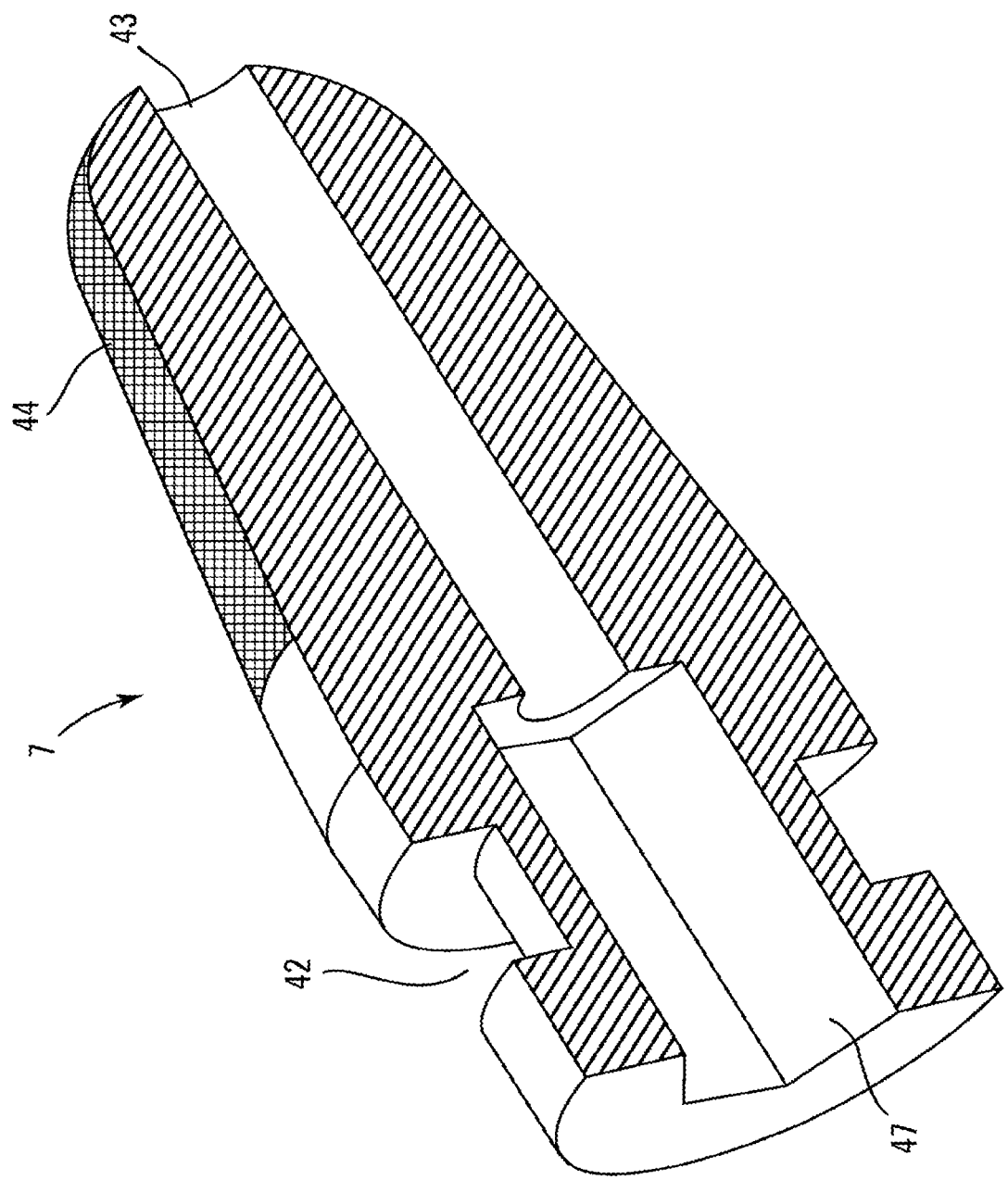
FIG. 6 is a perspective, section of a rotating tip element of the catheter.

Any of the catheter embodiments disclosed herein may be provided with either a stationary tip or a rotating tip depending on the application. An example of such a tip 7 is shown in FIG. 6. As previously described, the drive shaft 20 is connected or in some manner coupled to cutting element drive adapter 41 to form a rotatable assembly. Cutting element drive adaptor 41, shown in FIG. 5, has a hexagonal male portion 27. The hexagonal male portion of the cutting element drive adapter 41 mates with a female hexagonal adapter socket 47 of rotating tip element 7 (as shown in FIG. 2B) to couple the rotating tip to the rotatable assembly when the cutting element 4 is in the retracted position. When the cutting element is in the cutting position the rotatable tip is uncoupled from the drive assembly. In other words, the mating portions of the cutting element drive adaptor (drive assembly) and the rotatable tip form a connector assembly for selectively coupling and uncoupling the rotatable tip from the rotatable assembly. The retracted position is achieved by moving lever 13 to the forward position. When the drive shaft is rotated while the cutting element is in the retracted position the rotational motion is imparted to the cutting element drive adaptor which, in turn, rotates the rotating tip 7. As shown in FIG. 6, rotating tip 7 includes an optional lumen 43 extending from socket 47 to its distal end. Lumen 43 aligns with lumen 28 of the cutting element drive adaptor 41 when the cutting element is in the retracted position to accommodate a guidewire. Thus, the guidewire lumen for this over-the-wire type catheter comprises the internal lumen of the hollow drive shaft, lumen 28 of the cutting element drive adaptor and lumen 43 of the rotating tip. It should be recognized that although the mating portions of the cutting element drive adaptor and tip are shown in this embodiment as being hexagonal in cross-section, other cross-sectional shapes such as square, triangular and the like could also be chosen, so long as the mating relationship between the parts is rotationally secure. It should also be recognized that in embodiments of the catheter having a stationary tip the cutting element drive adaptor can be modified to not include the hexagonal male portion or any other structure which mates with the tip.

Rotating tip 7 is coupled to the catheter housing by a retention collar 35 (FIG. 2B). Retention collar 35 is fixedly attached to the catheter body 8 by means of rivets, welding, adhesive and the like. Retention collar 35 is accepted in a retention cavity 42 of rotating tip element 7 (see also, FIG. 6). Retention collar 35 prevents axial movement of rotating tip 7 while at the same time allowing free rotational movement of the tip. When the cutting element is in the retracted position and the cutting element drive motor is energized to rotate drive shaft 20, the hexagonal male portion 27 of cutting element drive adapter 41, which is accepted into the adapter socket 47 of the rotating tip element 7, also rotates, thus rotating the abrasive rotating tip 7. Retention collar 35, which is accepted into the retention cavity 42, allows the rotating tip element 40 to freely rotate while maintaining a secure attachment of the rotating tip element 40 to the catheter 2.

The outer distal surface of the rotating tip element 7 may have a roughened abrasive surface 44 which may be comprised of hard, particulate materials such as diamond, silicon carbide, aluminum oxide, tungsten carbide, metal, hardened steel or other materials, having a range of particle sizes and may be defined by grit size. During use, as the catheter is distally advanced through the lumen of the vessel, an occlusion or blockage such as a chronic total occlusion (CTO) may prevent the catheter from progressing. In this instance the rotating tip 7 would be engaged and begin to rotate and the roughened abrasive surface 44 would begin to shear away layers of the CTO, or other blockage, until the rotating tip 7 bores through the CTO (or other blockage) enabling the catheter 2 to be advanced to position the cutting window at a location allowing material to be removed by the cutting element from the lesion at the treatment site. As mentioned previously, the catheter body may be provided with a side wall opening at a proximal location which can be connected by tubing to a suction source so that debris created by the rotating tip can be aspirated through the annular space between the catheter body and the drive shaft.

In use, catheter 2 cuts softer atheroma from a vessel wall in relatively large strips and cup shaped surface 24 directs these strips through opening 6 into collection chamber 12. Since collection chamber 12 is positioned proximal of window 6 and cutting element 4 it is desirable to keep the passageway between window 6 and the collection chamber as free from obstruction as possible. One potential obstruction which could hinder the movement of cut material from the window to the collection chamber is the drive shaft. As explained above, the cutting element is tilted in the direction of the window in order to extend the cutting edge out of the window during the cutting procedure. This tilt also affects the position of the drive shaft and tends to redirect a portion of the drive shaft just proximal to the cutting element in the direction of the window. The amount of obstruction caused by this deflection of the drive shaft when the cutting element is tilted is minimized by making the drive shaft extremely flexible over its length or, in another embodiment, over the length of the drive shaft immediately proximal to the cutting element. For example, a flexible drive shaft will bend sharply adjacent its connection or coupling point with the cutting element so that it maintains a position close to the central axis of the catheter 2. Increased flexibility of drive shaft 20 also reduces any resistive force of the drive shaft to the angular tilt the cutting element 4. In drive shafts formed from solid hollow tubular material, the drive shaft may be provided with spiral (or otherwise directed) cuts S, which may be formed mechanically by a laser as seen in cross section in FIG. 4A. In some embodiments the spiral cuts are made in a direction that tightens when the shaft is rotated and make connecting shaft 20 more flexible along the spiral cut portion just proximal to the coupling point with cutting element. These spiral cuts allow the cutting element to tilt freely outside opening 6 while the position of the drive shaft 20 may be maintained within the housing and out of the way of material being cut by cutting element 4 and directed into collection chamber 12.

Figure 13:
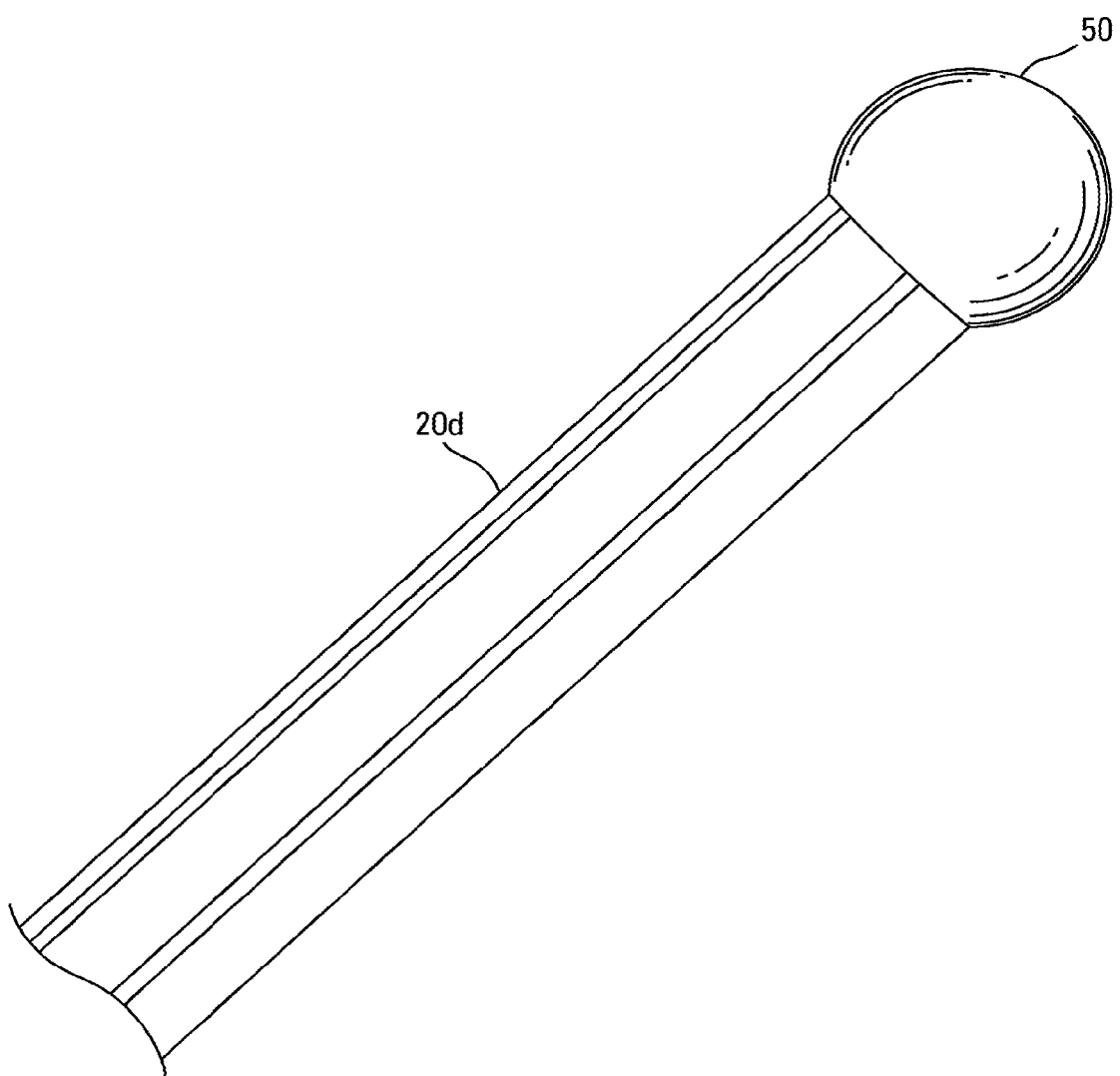
FIG. 13 is a partial view of a drive shaft.
Figure 14:
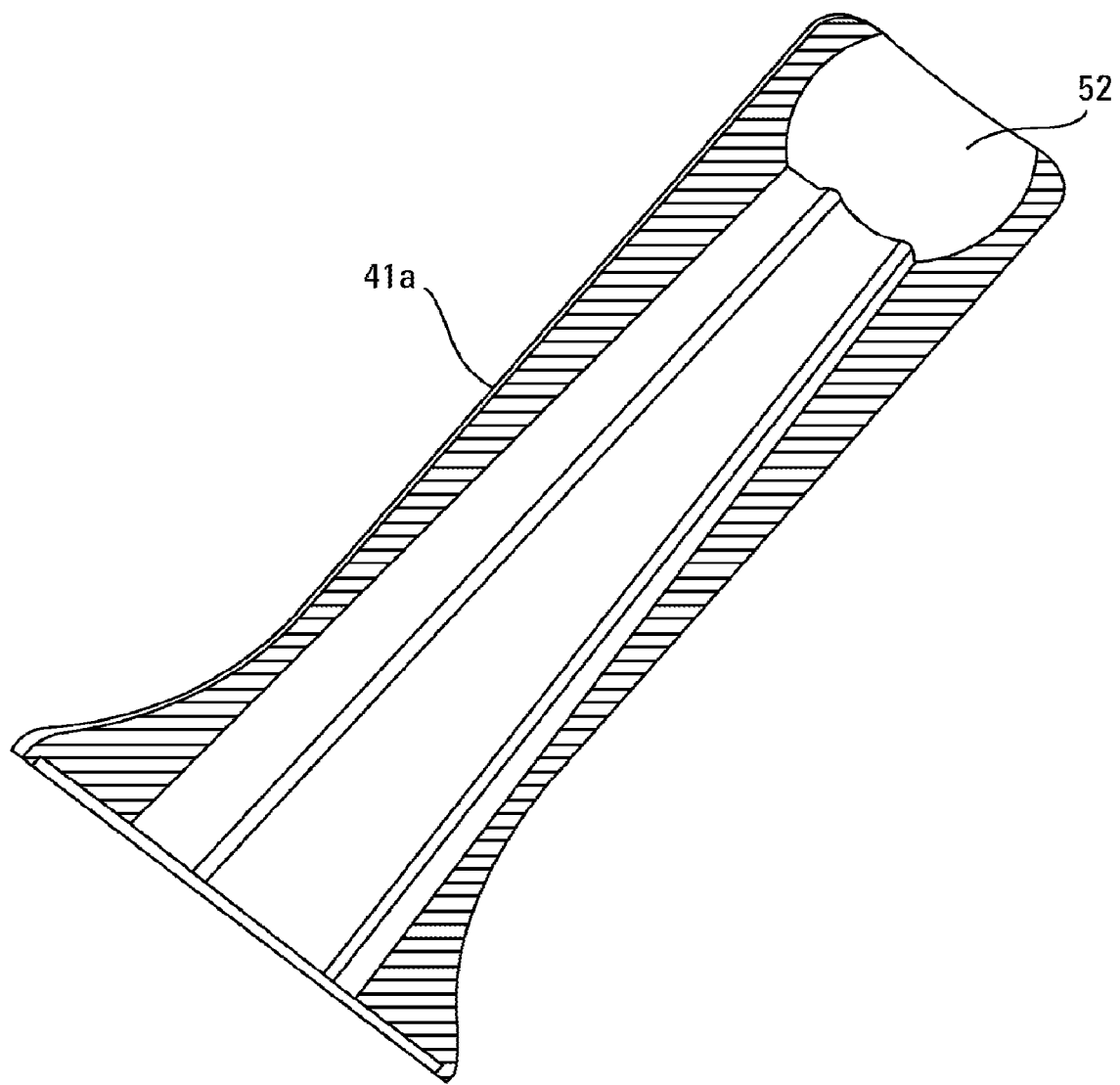
FIG. 14 is a partial view of a drive adaptor for use with the drive shaft of FIG. 13.
Figure 15:
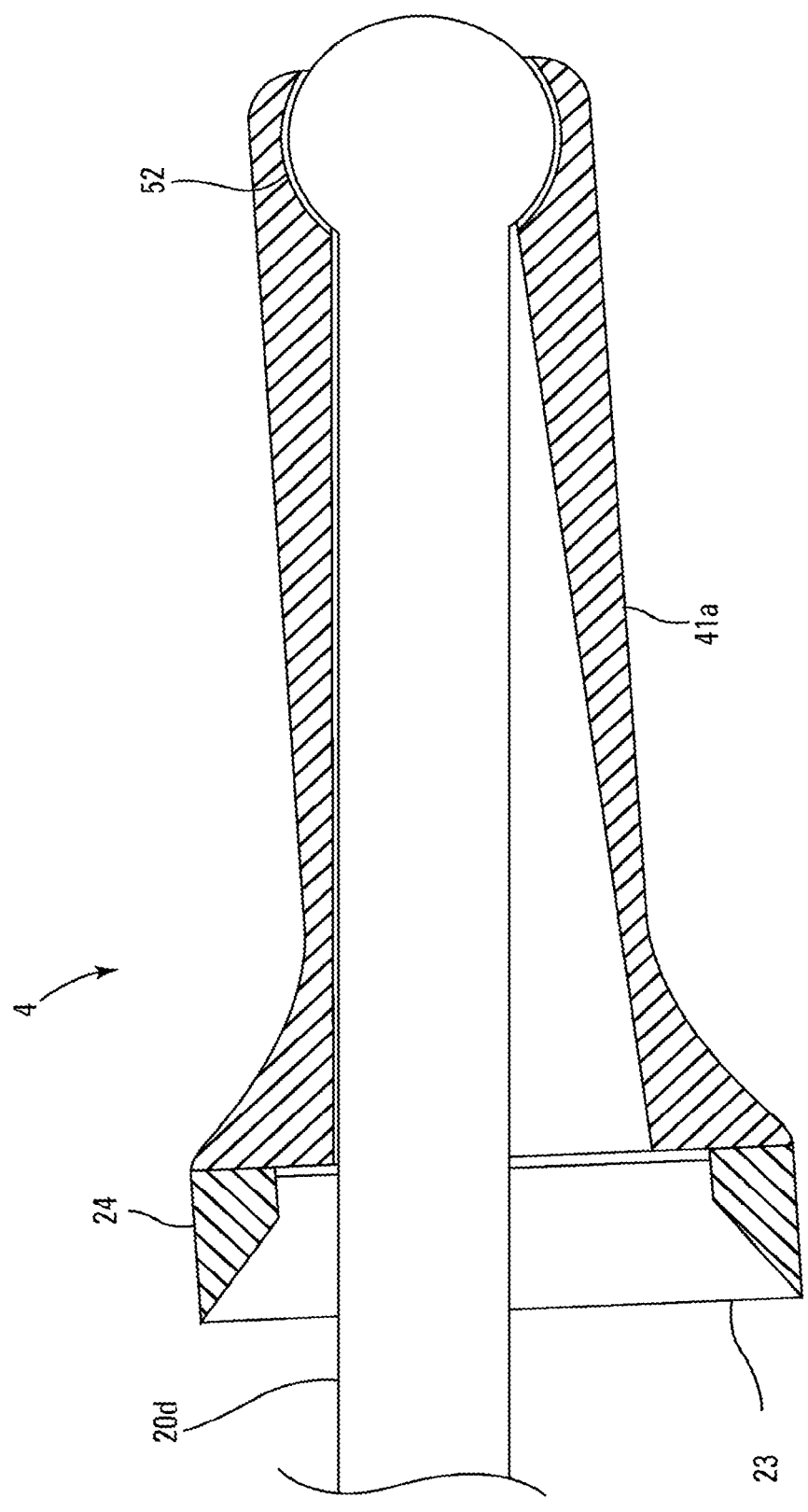
FIG. 15 is a partial longitudinal section of the cutting element drive adaptor with the drive shaft received therein.

In an alternative embodiment shown in FIGS. 13 to 15 the drive shaft and cutting element may be modified to further ensure that the drive shaft does not obstruct the passageway between the window and the collection chamber. An alternative drive shaft 20d has an enlarged ball 50 at its distal end. An alternative cutting element drive adaptor 41a has a socket 52 at its distal end that is shaped to receive the enlarged ball 50 of drive shaft 20d. A distal region of drive shaft 20d adjacent enlarged ball 50 has a hexagonal cross-sectional shape. Cutting element drive adaptor 41a includes a lumen which tapers inwardly from the proximal end to socket 52. The tapering shape is configured to match the cross-sectional shape of the drive shaft adjacent the enlarged ball. In this embodiment the connection between the drive shaft and the cutting element drive adaptor is mechanical. Ball 50 is securely retained within socket 52 and prevents any longitudinal movement of the drive shaft with respect to the cutting element drive adaptor. The tapered internal sides of the cutting element drive adaptor are sized to prevent the drive shaft from rotating with respect to the cutting element drive adaptor. However, the tapered internal sides of the cutting element drive adaptor are sized to allow some pivoting movement of the drive shaft with respect to the cutting element drive adaptor. This configuration allows the cutting element drive adaptor 41a to receive and be rotated by drive shaft 20d while at the same time permitting the cutting element drive adaptor to tilt or pivot about enlarged ball 50. Thus, in this embodiment, when cutting element drive adaptor 41a is tilted toward the cutting window to expose the cutting element through the window in the manner previously described, the drive shaft is configured to remain centered within the catheter body or is at least not urged toward the window to a substantial degree. This embodiment thus reduces potential interference of the drive shaft with cut material passing from the cutting window to the collection chamber.

Figure 7:
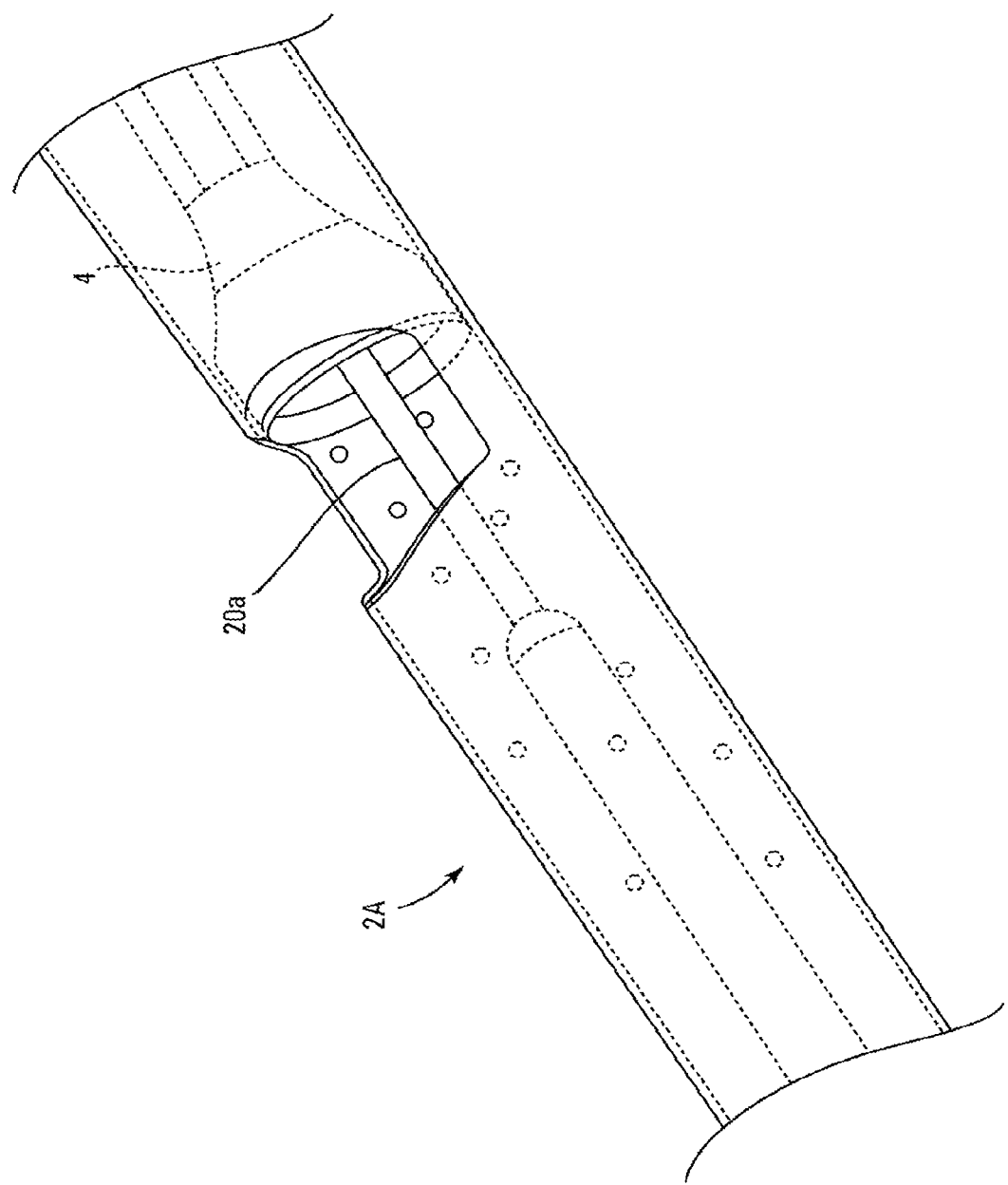
FIG. 7 is a perspective of a portion of the catheter with an alternate embodiment of the drive shaft.
Figure 8:
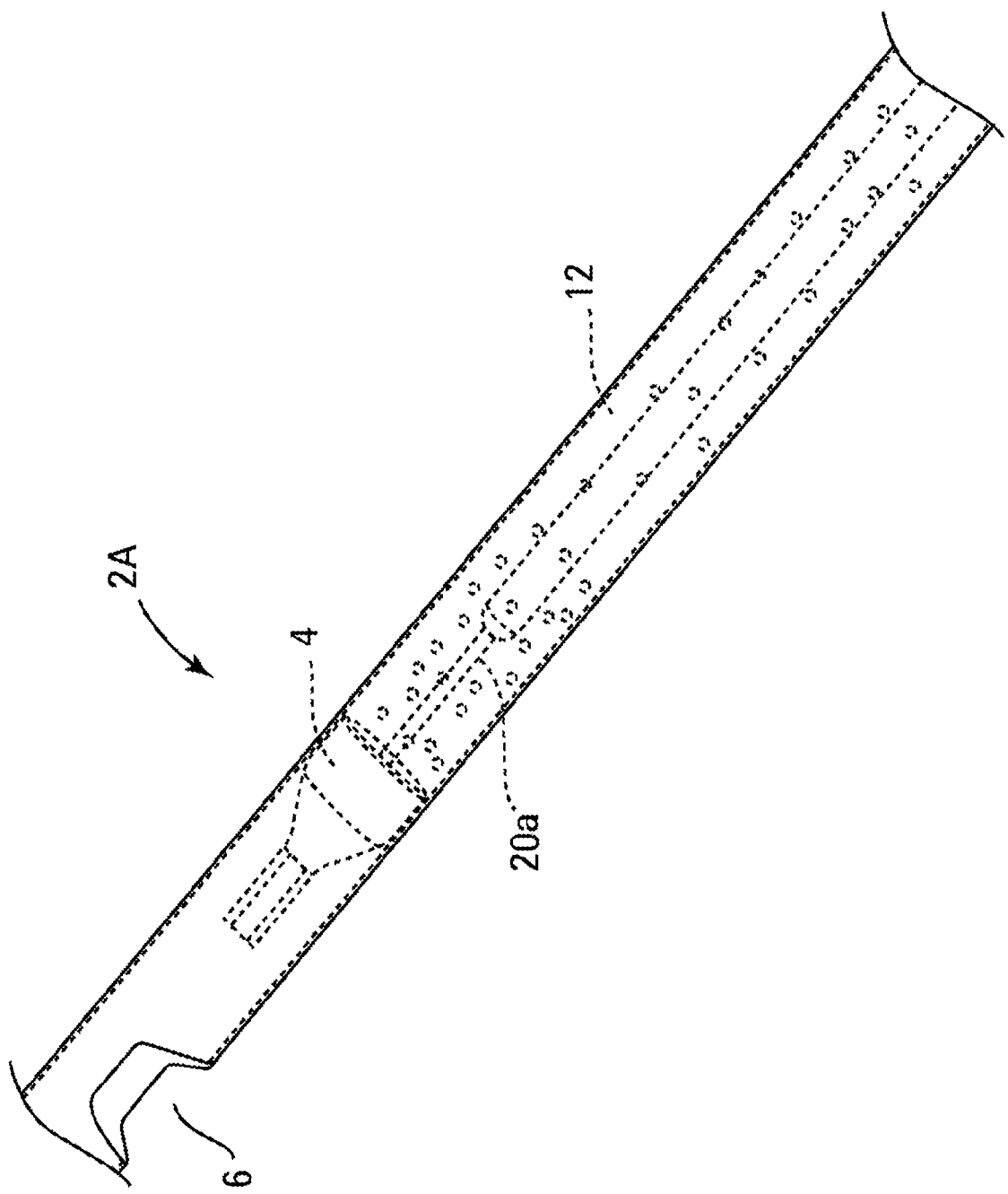
FIG. 8 is an elevation of the portion of the catheter shown in FIG. 7 including a material collection feature.

An alternative catheter embodiment is shown in FIGS. 7 and 8. Catheter 2A is shown wherein the same or similar reference numbers of catheter 2A refer to the same or similar structures of catheter 2 and all discussion concerning the same or similar features of catheter 2 are equally applicable here unless noted otherwise. Compared to catheter 2, drive shaft 20a has been given a narrowed diameter immediately proximal to the cutting element 4. This narrowed diameter presents less obstruction to the passage of material from cutting window 6 to collection chamber 12. Thus, catheter 2A allows for greater ease of collecting atheroma/tissue at a treatment site by providing additional space for the atheroma/tissue to be collected inside the catheter. It should be noted that the drive shaft 20a (or the drive shafts of any of the other embodiments disclosed herein) could be additionally coated with a lubricant or Teflon to reduce atheroma/tissue from sticking to the drive shaft 20a.

FIG. 8 shows catheter 2A which is provided with features that enhance the material storage efficiency of the collection chamber. In this embodiment the handle or control mechanism is modified to allow the drive shaft to be withdrawn further proximally resulting in the cutting element being withdrawn proximally past the cutting window. In this embodiment lever 16 is advanced distally thereby advancing bushing 31 distally and allowing cutting element 4 to return within the catheter body so the cutting element does not extend through the cutting window. The drive shaft and cutting element 4 are then pulled back proximally toward the operator while the catheter and housing remain stationary. When the cutting element is pulled back proximally past the cutting window the cup shaped surface 24 collects and pulls back the atheroma/tissue within the lumen of the catheter into the collection chamber 12. This compresses the atheroma/tissue and adds further material storage capability to catheter 2A. The pull back compression step can be done while the cutting element is being rotated although it will typically be done without rotation of the cutting element. It should be noted that this pull back compression system could be incorporated into any of the catheter embodiments disclosed herein for the purpose of increasing the storage efficiency of the collection chamber.

Figure 9:
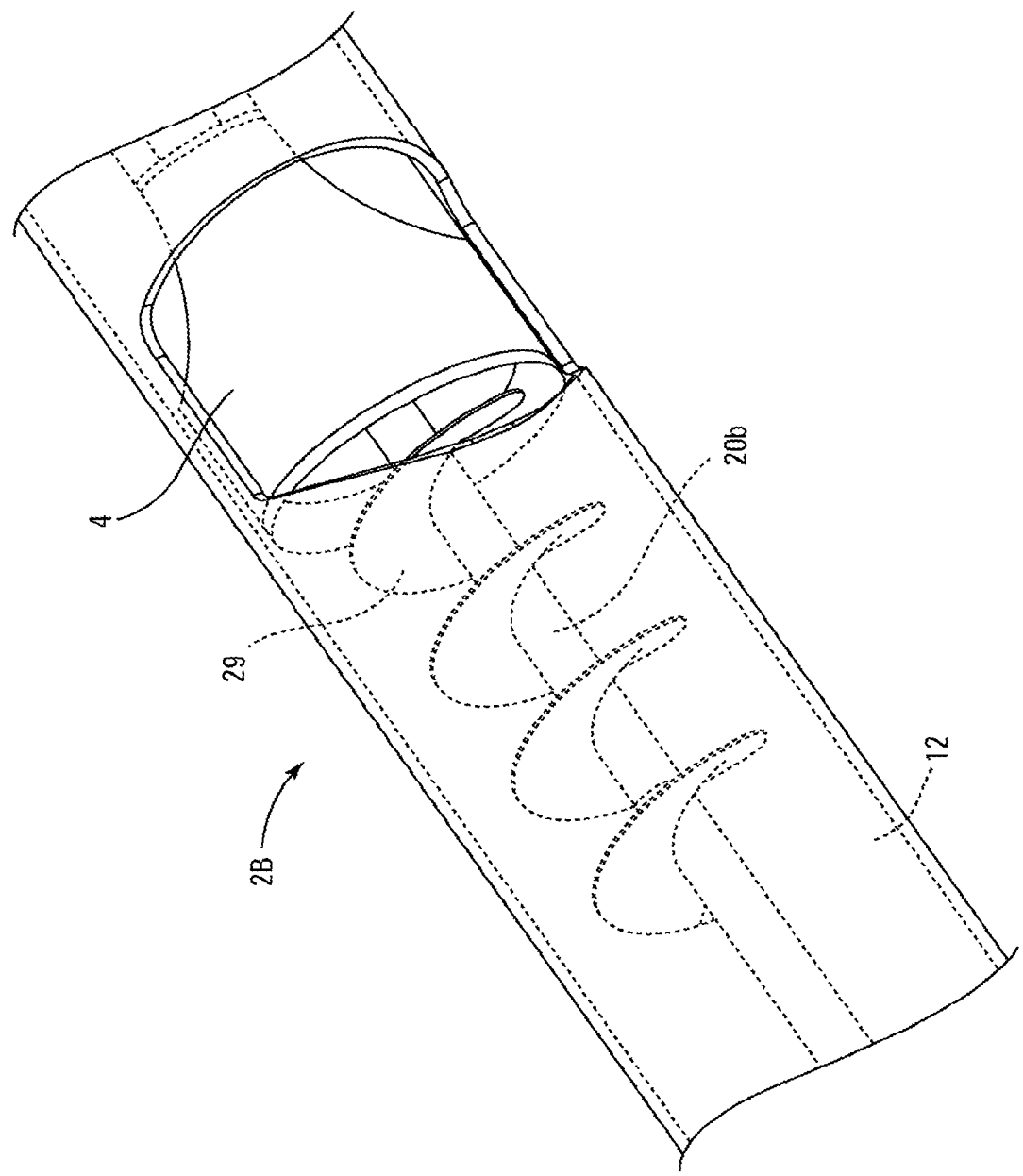
FIG. 9 is a perspective of a portion of the catheter with an alternate embodiment of the drive shaft.

Another embodiment of the catheter is shown in FIG. 9. Catheter 2B is shown wherein the same or similar reference numbers of catheter 2B refer to the same or similar structures of catheter 2 and all discussion concerning the same or similar features of catheter 2 are equally applicable here unless noted otherwise. Compared to catheter 2, drive shaft 20b has been provided with an external helical thread 29 immediately proximal to the cutting element 4. As the thread 29 rotates along with drive shaft 20b, atheroma/tissue entering the cutting window is pulled away from the cutting area and treatment site and into the collection chamber 12 of catheter 2B. This embodiment provides greater ease of collecting atheroma/tissue at a treatment site by providing additional space for the atheroma/tissue to be collected inside the catheter. It should be noted that the connecting shaft 20b and thread 29 could be additionally coated with a lubricant or Teflon to reduce atheroma/tissue from sticking to the drive shaft 20b. In this embodiment the cutting element may be elongated and have the features of cutting element 4c described below in connection with FIGS. 10 to 12. As discussed previously, suction may be provided through catheter 2 to assist with drawing material proximally from the cutting element to thread 29.

Figure 10:
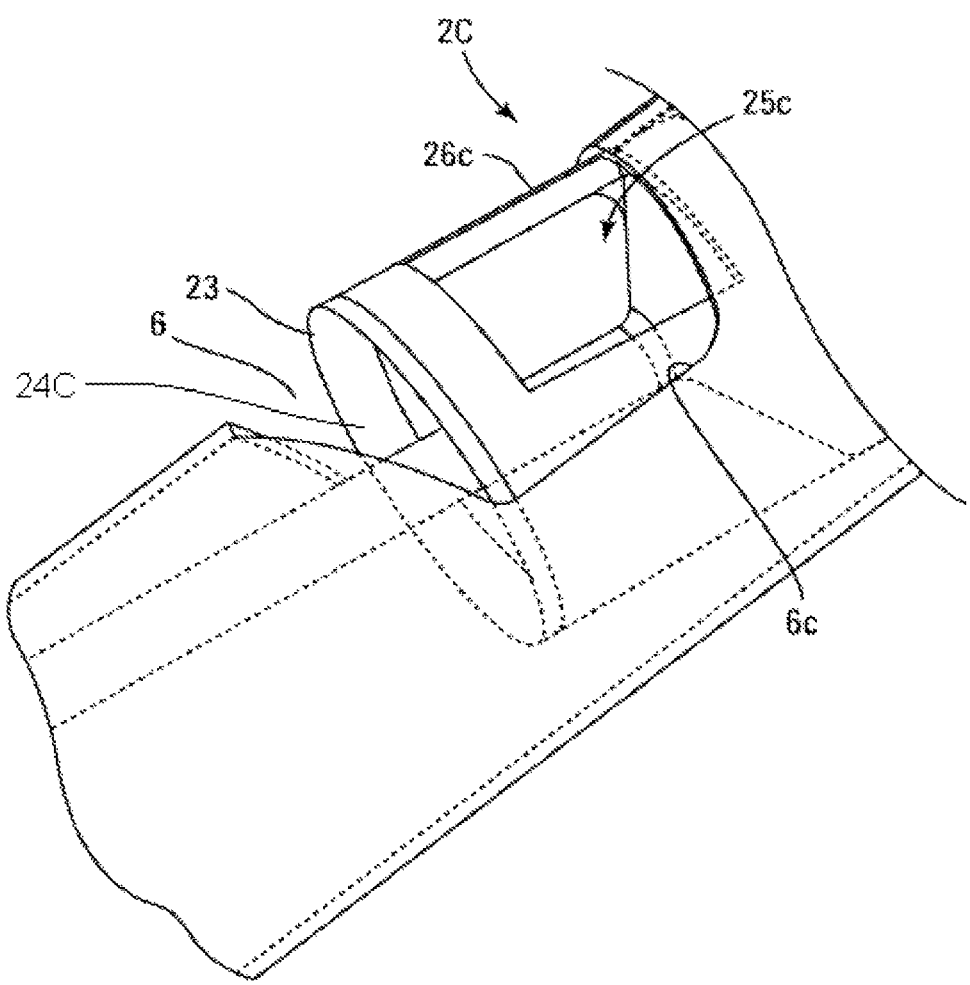
FIGS. 10 to 12 are fragmentary side elevations of catheter showing an alternate embodiment of a cutting element.
Figure 11:
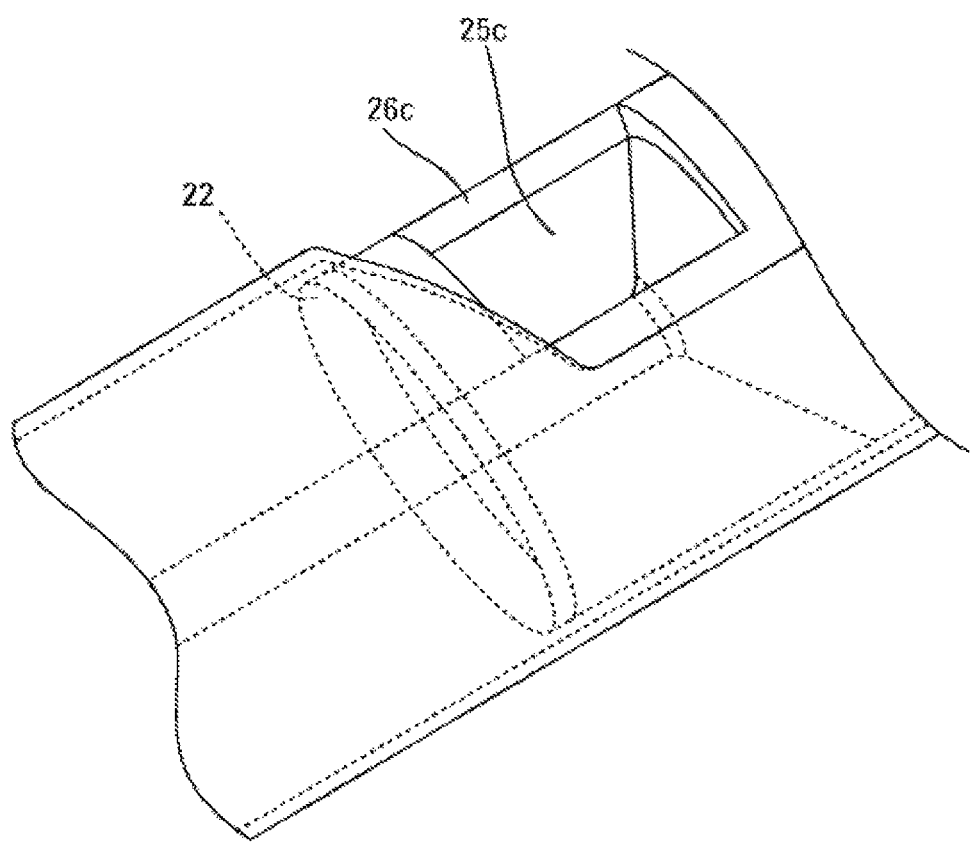
Figure 12:
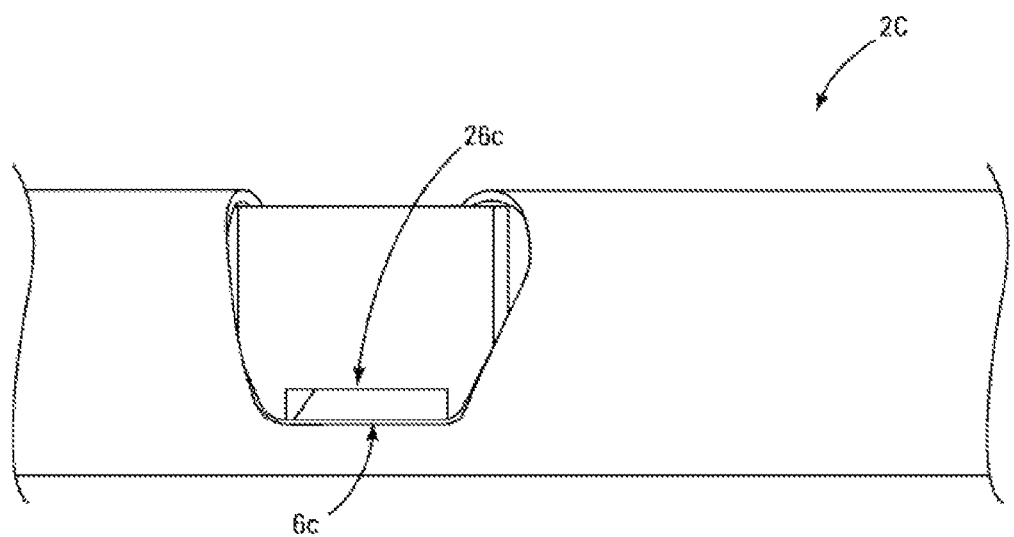

FIGS. 10 to 12 show another catheter embodiment. Catheter 2C is shown wherein the same or similar reference numbers of catheter 2C refer to the same or similar structures of catheter 2 and all discussion concerning the same or similar features of catheter 2 are equally applicable here unless noted otherwise. Compared to catheter 2, catheter 2C has an elongated cup shaped surface 24c of the cutting element 4c with a larger radial surface area than previously described corresponding cup shaped surfaces of cutting element 4. Additionally the elongated cup shaped surface 24c has an opening 25c with side cutting blade 26c which aids in material collection capability. Thus, cutting element 4c has two separate cutting structures and cutting positions. In the first cutting position as shown in FIG. 10, cutting element 4c is angularly extended through opening 6 as discussed above. In this position cutting edge 22 extends beyond and through cutting window 6. In this position the cutting is accomplished in the same manner as described with respect to catheter 2. Specifically, catheter 2C is pulled proximally through the vessel across the treatment site (lesion) to cut plaque from the lesion. Additionally, catheter 2C can be advanced distally while material is cut by cutting blade 26c, which enters through opening 25c. The material that enters opening 25c will be pushed proximally by additional material that enters opening 25c and will then get transported proximally by any of the tissue transportation methods discussed herein, including by suction and/or by thread 29 if provided. In the second cutting position as shown in FIGS. 11 and 12, the cutting element 4c is positioned within the cutting window but is not tilted outwardly. In this cutting position the cutting element 4c is rotated and any material from the vessel wall which invaginates the cutting window will be cut by side cutting blade 26c. Further, cutting window 6 may be provided with a cutting edge 6c against which cutting blade 26c acts to more efficiently cut the material. In this cutting position the catheter may remain stationary within the vessel or may be moved either proximally or distally during the cutting process. Although not shown, cutting element 4c includes a cutting element drive adaptor as shown in FIG. 5 if the catheter has an optional rotating tip or a modified cutting element drive adaptor if the catheter has a stationary tip.

Figure 16:
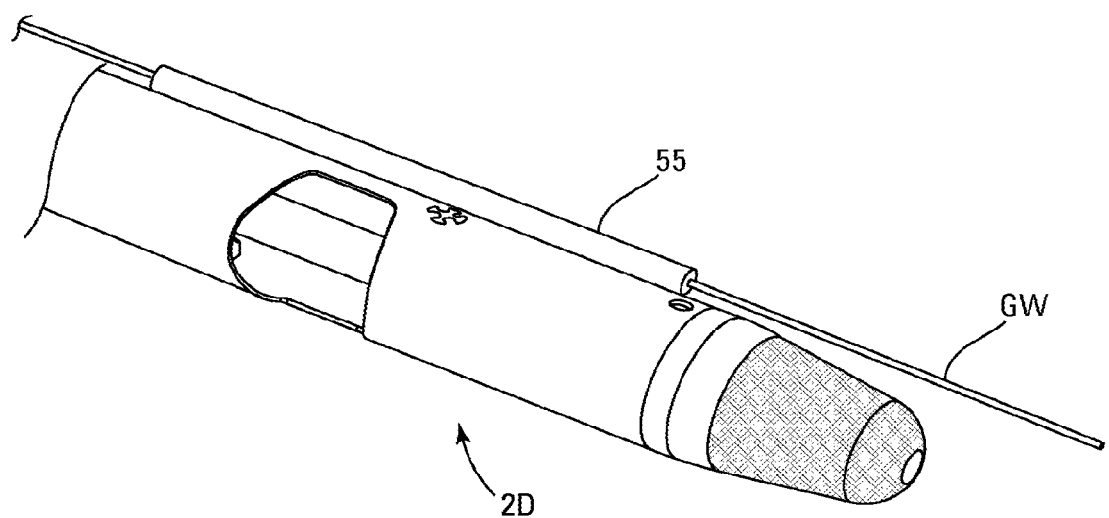
FIG. 16 is a fragmentary perspective of an alternative embodiment of the catheter configured for use as a rapid exchange catheter.

FIG. 16 shows an alternative embodiment of the catheter which has been constructed to be used as a rapid exchange catheter. Catheter 2D is shown wherein the same or similar reference numbers of catheter 2D refer to the same or similar structures of catheter 2 and all discussion concerning the same or similar features of catheter 2 are equally applicable here unless noted otherwise. Catheter 2D includes a side mounted tubular portion 55 which forms a relatively short guidewire lumen for receipt of a guidewire GW. Side mounted tubular portion 55 may be 1 to 30 cm long depending upon the application and is positioned not to interfere with cutting window 6. Additionally, side mounted tubular portion 55 is not attached to rotating tip 7, if the catheter is provided with a rotating tip.

Methods of using the catheters described herein are shown in FIGS. 17A, 17B, and 17C. A guidewire (GW) is percutaneously introduced into a patient's body and advanced to a region of interest in a patient's blood vessel V. If the treatment site (T) is a CTO, as shown in FIG. 17A, the guidewire may be unable to cross the lesion or occlusion material (M). FIG. 17A illustrates a totally occluded lumen in which a guidewire (GW) has been advanced to the proximal side of the occlusion material (M) of the treatment site (T). Catheter 2 has been advanced over the guidewire to a position just proximal of the occlusion material (M). During advancement the cutting element is in its retracted position. In order to enable the catheter 2 to treat this occlusion it must first cross the occlusion. With catheter 2 the occlusion material (M) may be crossed by energizing the drive motor to rotate the drive shaft. Rotation of the drive shaft with the cutting element in the retracted position causes the abrasive tip 7 to rotate. The abrasive surface on tip 7 cuts through even calcified material enabling the catheter to be slowly advanced through the lesion or occlusion material (M) until the cutting window 6 is adjacent the distal end of the lesion as shown in FIG. 17B. The material cut by the rotating tip may be aspirated through the lumen of the catheter body as previously described. With catheter 2 in the position shown in FIG. 17B lever 13 of handle 5 is moved from the forward position to the rearward position which results in the cutting element moving proximally from the retracted position to the cutting position. With the cutting element in this position pull wire 30 is pulled proximally to cause the tilt bushing 31 to move proximally with respect to ramp surface 14 of the cutting element drive adaptor. This results in cutting element 4 being tilted outwardly in the manner described previously to expose the cutting edge out the cutting window. When the cutting edge is exposed the catheter 2 is pulled proximally across the lesion to cut material from the lesion as shown in FIG. 17C. The cut material is directed through the cutting window and into the collection chamber. This cutting process can be repeated by advancing and retracting the catheter across the treatment site until a sufficient amount of material has been removed. At any time during the procedure, debris may be suctioned through the catheter or fluid may be introduced to the vessel through the catheter. Additionally, at any time during the procedure the guidewire may be removed and debris may be suctioned through the guidewire lumen or fluid may be introduced to the vessel through the guidewire lumen.

Although the method of use has been described with respect to catheter 2 the procedure for use of catheters 2A, 2B, 2C and 2D is similar. For example, catheter 2A, shown is FIGS. 7 and 8, is used in a similar manner. The narrowed diameter of the drive shaft immediately proximal to the cutting element allows the cutting element to tilt through the cutting window without causing the drive shaft to move laterally which might obstruct the window. Further, during use the cutting element of catheter 2A can be withdrawn proximally to pack material which has been cut and then moved distally back to the cutting position. Catheter 2B, shown in FIG. 9, is used in a similar manner with the additional feature that the drive shaft thread 29 pulls cut material entering the cutting window proximally to reduce the possibility of the cutting window becoming obstructed with cut material during the cutting process. Catheter 2C, shown in FIGS. 10 to 12 may be used in the manner described above. Specifically, in the first cutting position catheter 2C can be moved across the treatment site in a proximal direction to cut material with cutting edge 22 and can be advanced distally across the treatment site to cut material with cutting blade 26c. Catheter 2C can be moved distally and proximally across the treatment site as many times as necessary to remove a desired amount of diseased material. Additionally, catheter 2C may be used with the cutting blade in the second cutting position as described above. In the second cutting position catheter 2C will cut material which invaginates the opening 25c while the catheter is stationary or while catheter 2c is moved distally or proximally across the treatment site. Catheter 2D, shown in FIG. 16, is used as described above except that it is advanced to the treatment site over a guidewire positioned in the guidewire lumen defined by side mounted tubular portion 55.

Figure 18:
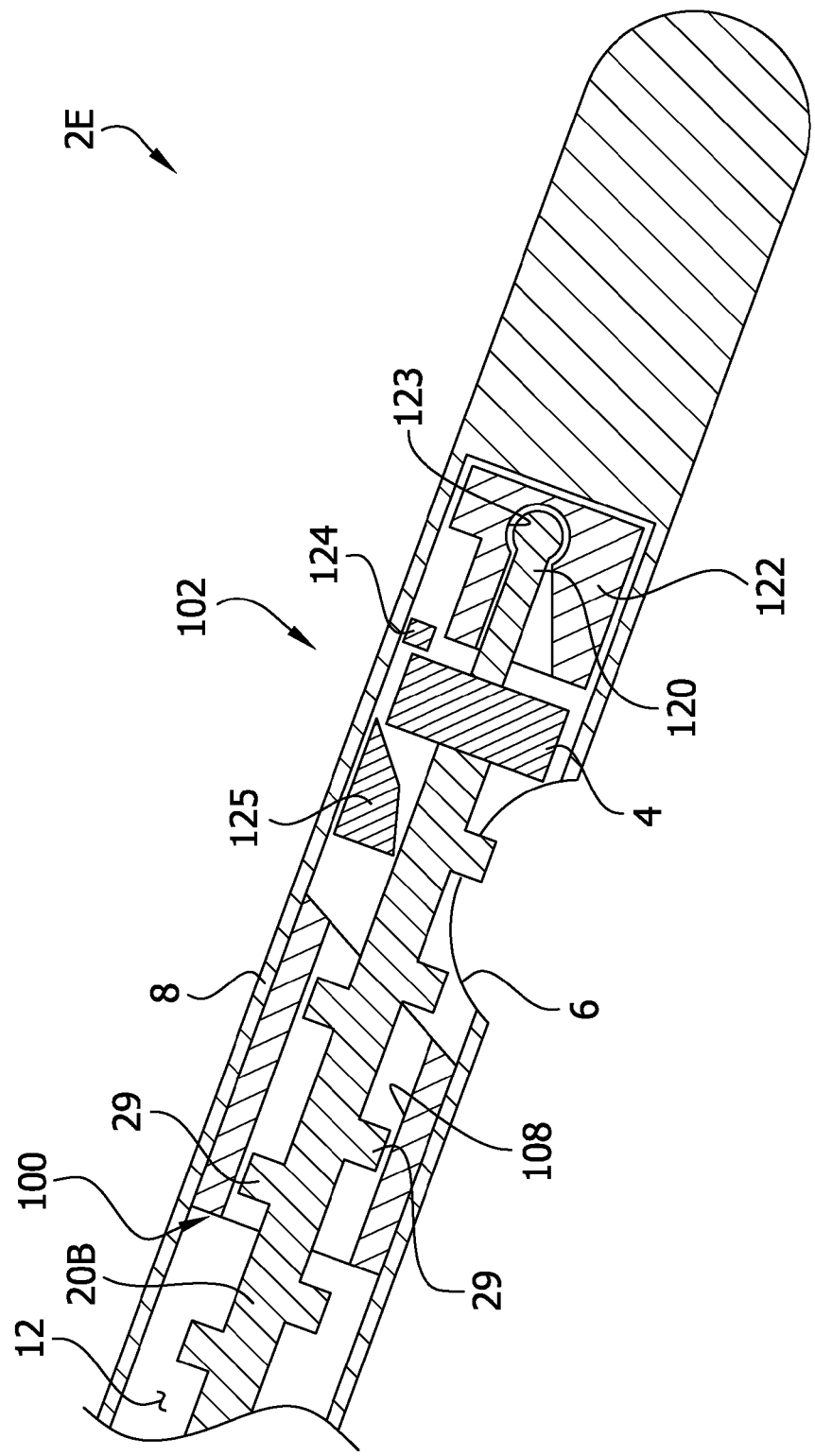
FIG. 18 is a longitudinal section of the distal end portion of another embodiment of the catheter, with a cutting element in a retracted position.
Figure 19:
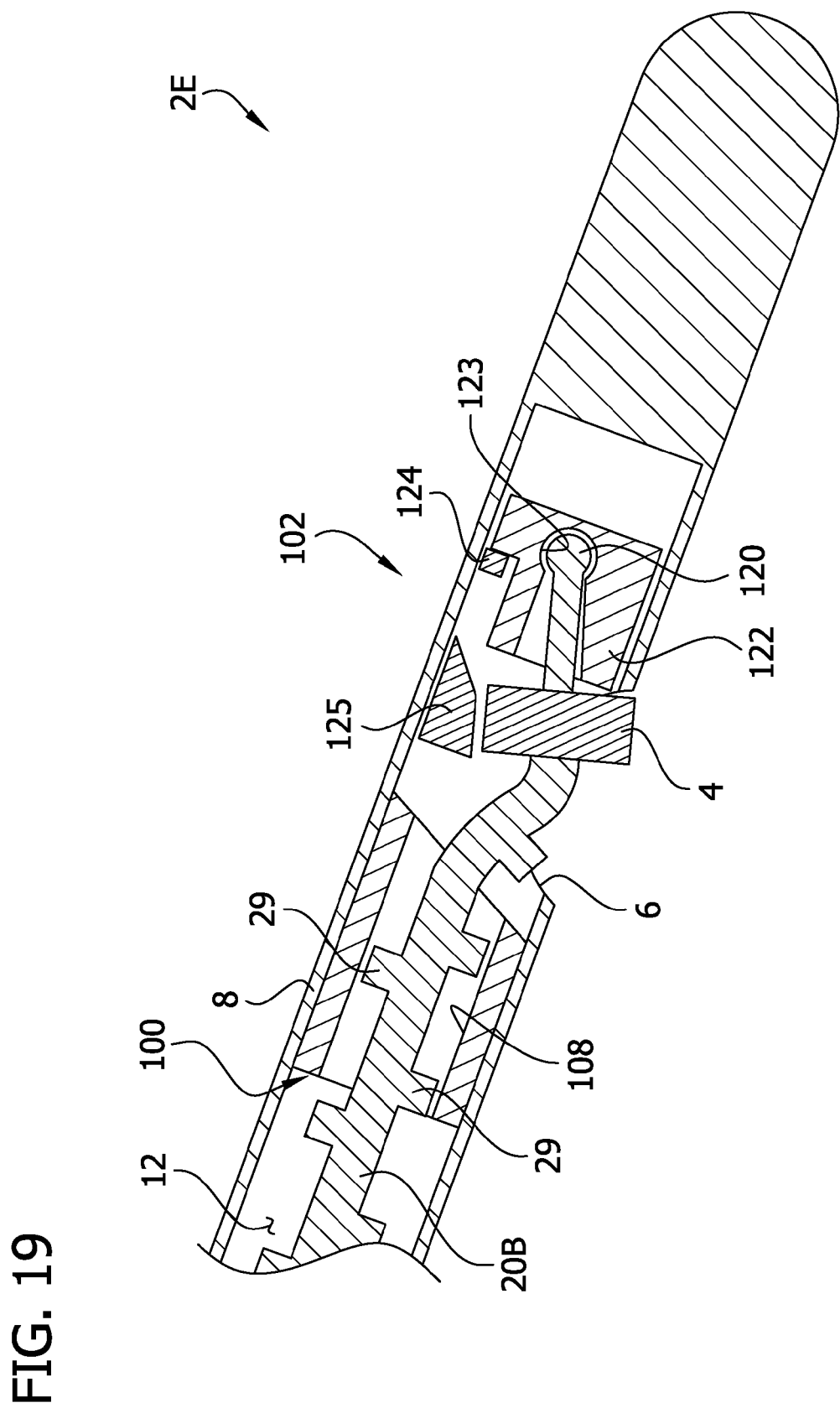
FIG. 19 is similar to FIG. 18, with the cutting element in a cutting position.
Figure 20:
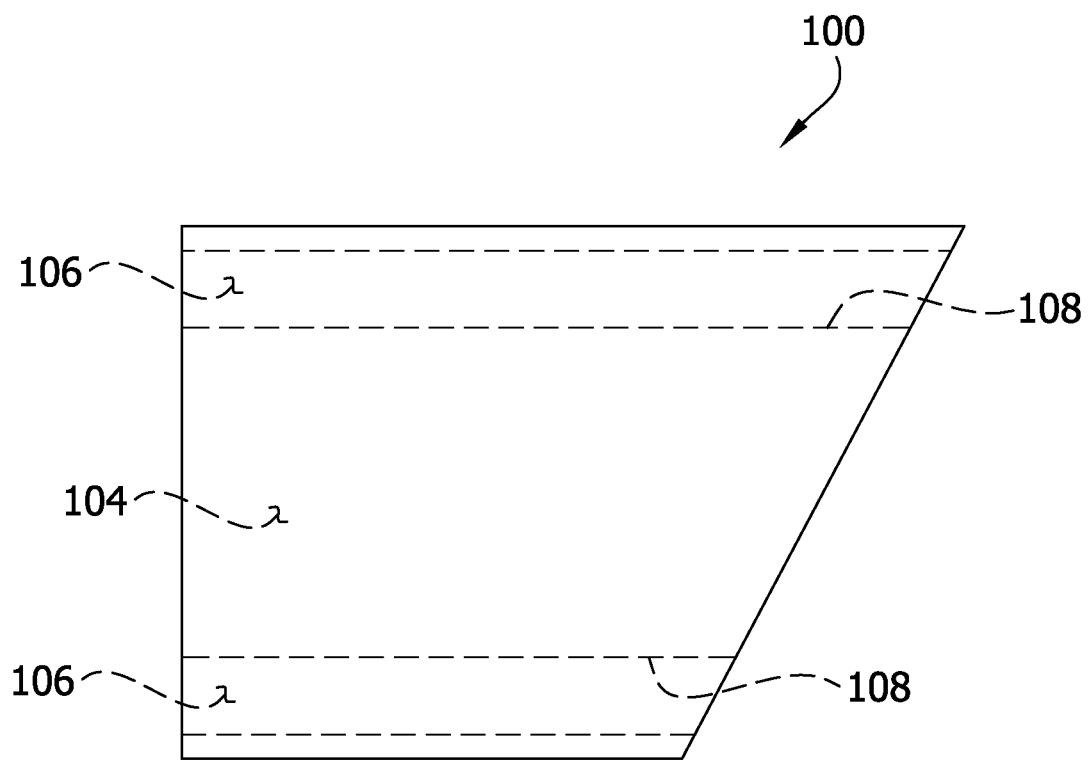
FIG. 20 is an enlarged side elevation of a shearing member of the catheter of FIG. 18.

Referring to FIGS. 18 and 19, another embodiment of a catheter, similar to catheter 2B, is generally indicated at 2E. The catheter 2E includes a shearing member, generally indicated at 100, disposed within the catheter body 8 adjacent and immediately proximal to the window 6. The catheter 2E also includes a deployment mechanism, generally indicated at 102, for selectively deploying (i.e., exposing) and retracting the cutting element 4. Other than these two differences, the present catheter 2E may be substantially identical to the catheter 2B. Accordingly, corresponding teachings set forth above for catheter 2B apply equally to the present catheter 2E, and like components are indicated by corresponding reference numerals.

Figure 21:
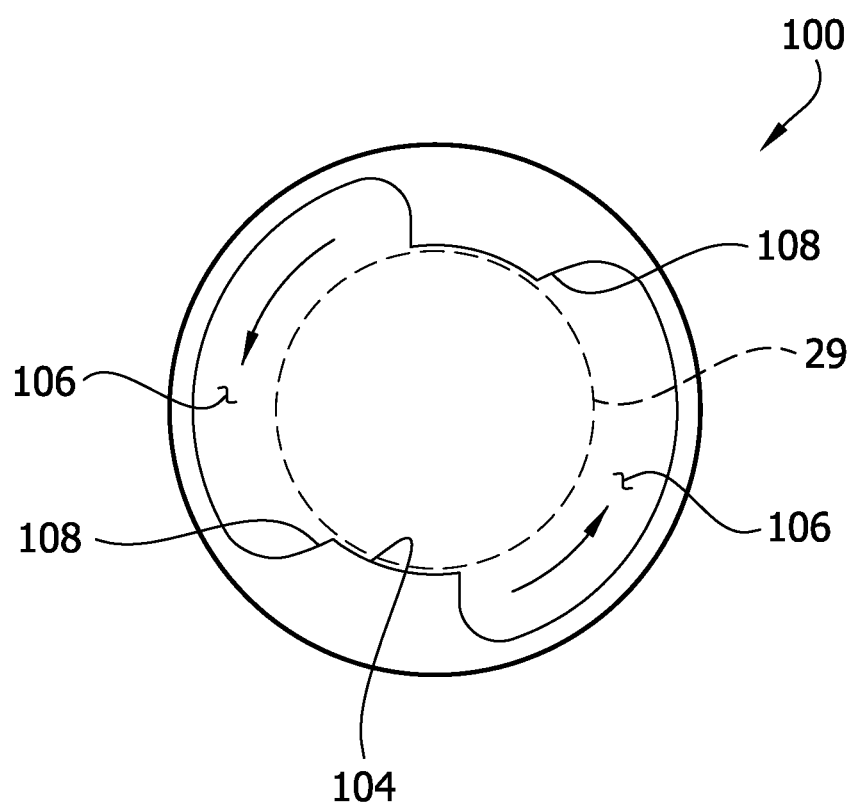
FIG. 21 is a front elevation of the shearing member.

Referring to FIGS. 18-21, the illustrated shearing member 100 defines a longitudinal bore 104 extending through proximal and distal ends of the shearing member and in communication with the tissue collection chamber 12 (or another internal passage in the catheter body 8). The drive shaft 20B passes through the bore 104 and the thread 29 on the drive shaft interacts with the shearing member 100 to move removed tissue proximally, as explained in more detail below. Circumferentially spaced apart longitudinal channels 106 extend longitudinally through an interior surface defining the bore 104 to form longitudinal shearing edges 108. The external thread 29 (as shown in broken lines in FIG. 21) on the drive shaft 20B interacts with the shearing edges 108 at the bore 104 as the cutting element 4 rotates (i.e., clockwise rotation as shown in FIG. 21) to shear and pinch removed material therebetween to facilitate proximal movement of the removed tissue within shearing member 100. In the present embodiment (shown best in FIG. 21), the major diameter of the drive shaft thread 29 is slightly less than the inner diameter of the bore 104, so that there is small radial gap (i.e., small amount of play) between the thread and the shearing edges 108. The radial gap is such so as not to inhibit or impede rotation of the drive shaft 20B in the bore 104, and at the same time, provide this shearing or pinching of removed material between the drive shaft thread 29 and the shearing edges 108 to facilitate proximal movement of the removed tissue. In addition, the channels 106 permit passage of larger pieces of tissue through the shearing member 100.

Figure 22:
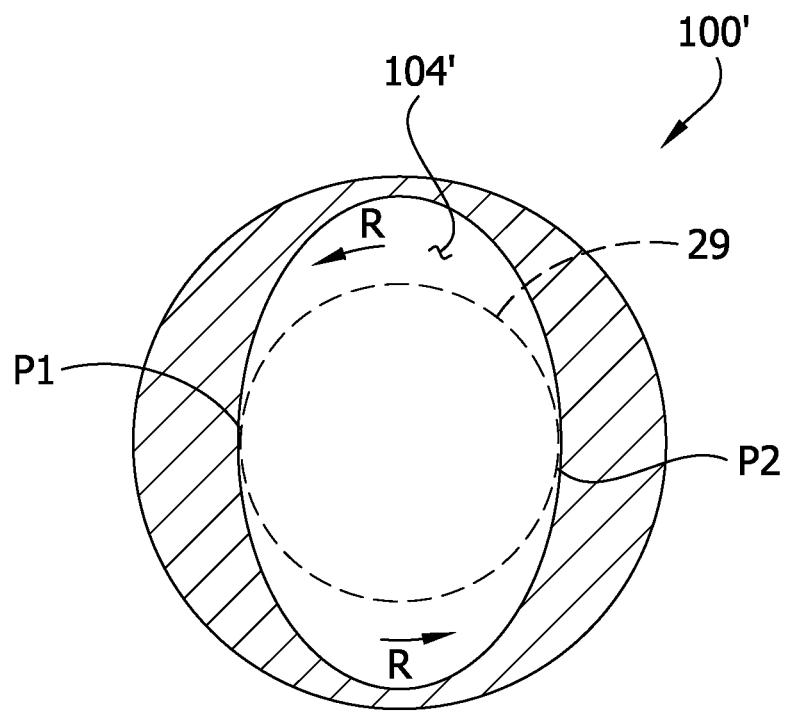
FIG. 22 is a front elevation of another embodiment of a shearing member.

The shearing member 100 may be of other configurations for use in moving removed tissue proximally within the catheter body. For example, referring to FIG. 22 a cross-sectional view of another embodiment of the shearing member is generally indicated at 100'. In this embodiment, the shearing member 100' defines a bore 104' having an oblong or oval cross-sectional shape. As shown in FIG. 22, the bore 104' is sized such that the drive shaft thread 29, which has a generally circular shape, interacts with the interior surface defining the bore generally at two shearing regions P1, P2 (forming shearing edges), as the drive shaft 20B rotates in the direction R. Thus, the thread 29 (as shown in broken lines in FIG. 22) on the drive shaft 20B interacts with the interior surface of the shearing member 100' at points P1, P2 as the cutting member 4 rotates to shear and pinch removed material therebetween to facilitate proximal movement of the removed tissue within shearing member 100'.

Referring again to FIGS. 18 and 19, as disclosed above the deployment mechanism 102 is different than the previous embodiment. In particular and as explained in more detail below, the cutting element 4 is pivotally secured to the catheter body 8 so that when the drive shaft 20B is moved proximally, in a longitudinal or axial direction, such as by moving the lever 13 on the handle proximally (lever 16 may be omitted), the cutting element pivots relative to the catheter body 8 toward the window 6 to expose at least a portion of the cutting edge 22 (see FIG. 19). Likewise, the cutting element 4 may be moved from its cutting position (FIG. 19) to its retracted position (FIG. 18) by moving the drive shaft 20B distally, such as by moving the lever 13 distally, such that the cutting element pivots relative to the catheter body 8 away from the window 6. Although not illustrated, the distal tip of the catheter body 8 (i.e., the portion of the catheter body located distal of the window 6) may be configured to deflect or pivot in a direction generally away from the window.

In the illustrated embodiment, the deployment mechanism 102 comprises a ball member 120 fixedly secured to and extending distally from the cutting element 4, and a socket member 122 defining a cavity 123 in which the ball member is received. The ball member 120 is constrained axially relative to the socket member 122 but is allowed to pivot within the cavity relative to the longitudinal axis LA of the catheter body 22. The cutting element 4, ball member 120, and socket member 122 are movable axially or longitudinally relative to the catheter body 8 as a unit or assembly. The ball member 120 may be formed integrally with the cutting element 4 or formed separated and secured thereto by suitable means. The ball member 120 is rotatable relative to the socket member 122 about the longitudinal axis of the cutting element 4. The deployment mechanism 102 also includes a stop 124 for restricting proximal movement of the socket member 122, and a ramp 125 to facilitate pivoting of the cutting element 4 relative to the catheter body 8. Each of these components is explained in more detail below.

In the illustrated embodiment, the cutting element 4, ball member 120, and socket member 122 are movable longitudinally as an assembly, such as by imparting longitudinal movement of the driveshaft 20B, to position the cutting element between its cutting position (FIG. 19) and its retracted position (FIG. 18). To position the cutting element 4 in its cutting position, the driveshaft 20B is moved proximally relative to the catheter body 8, thereby imparting proximal movement of the cutting element 4, ball member 120, and socket member 122 as an assembly. As the cutting element 4 moves proximally, it rides along the ramp 125 and the ball member 120 pivots within the socket member 122 so that the cutting element pivots toward the window 6 to expose a portion of the cutting edge 22 of the cutting element. The socket member 122 engages the stop 124 when the cutting element 4 is at its cutting position to inhibit further exposure of the cutting element through the window 6. To position the cutting element 4 in its retracted position, the driveshaft 20B is moved distally relative to the catheter body 8, thereby imparting distal movement of the cutting element 4, ball member 120, and socket member 122 as an assembly. As the cutting element 4 move distally, the ball member 120 pivots relative to the socket member 122 so that the cutting element pivots away from the window 6 and retracts back into the catheter body 8, whereby entirety of the cutting edge 22 is received in the catheter body. Another ramp (not shown) may be provided adjacent the window 6 so that the cutting element 4 rides along the ramp to facilitate pivoting of the cutting element away from the window.

Figure 23:
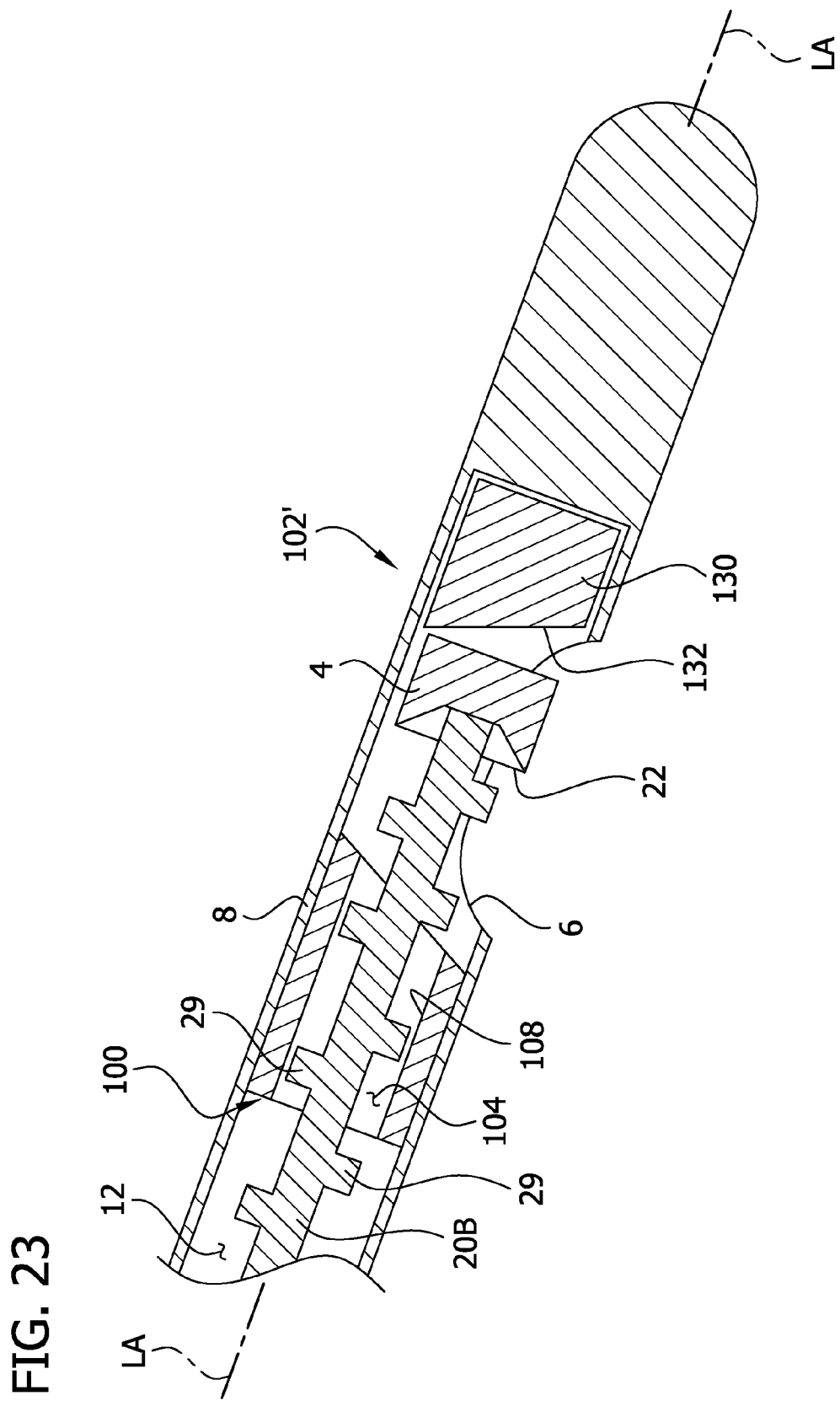
FIG. 23 is similar to FIG. 18, but with a different deployment mechanism.
Figure 24:
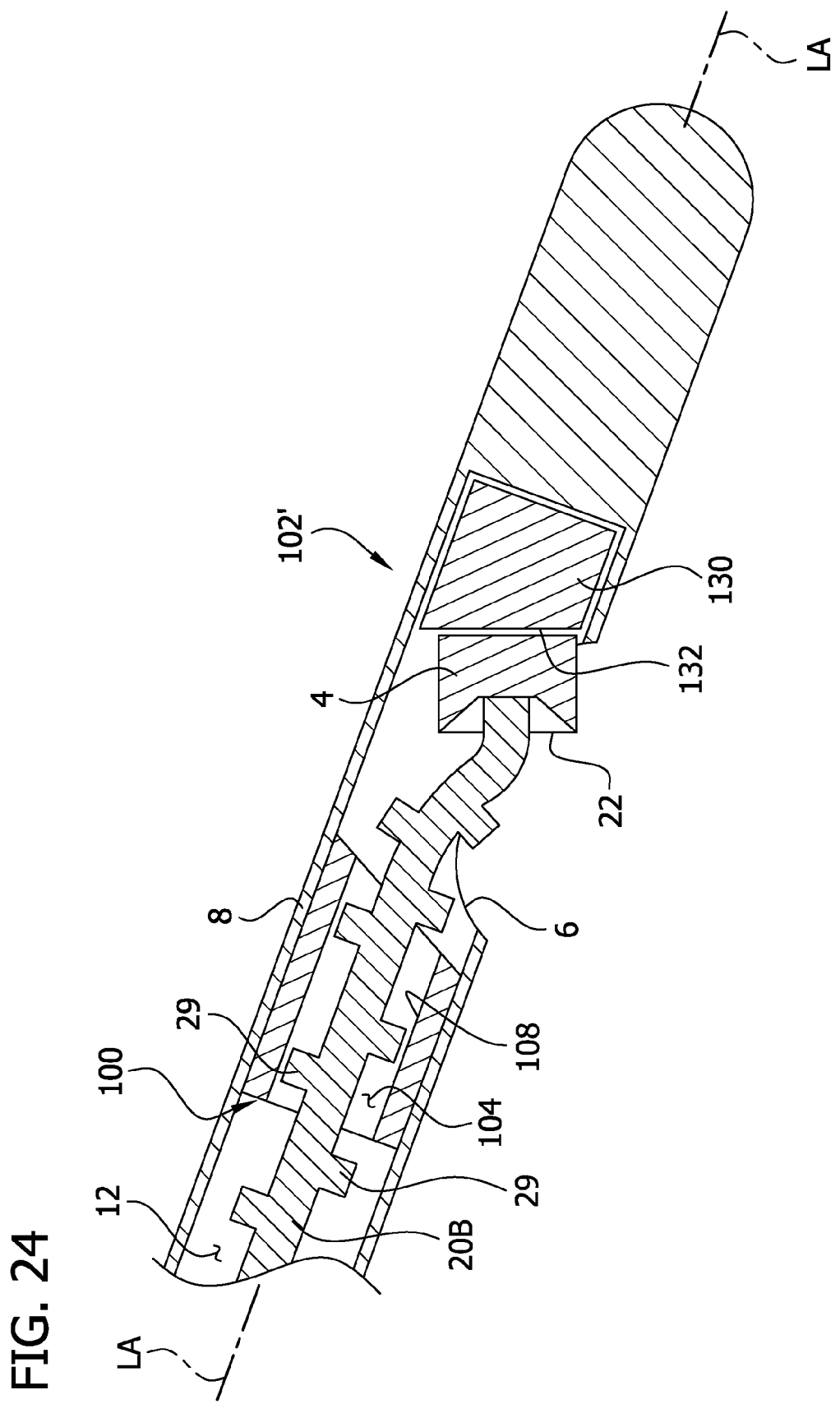
FIG. 24 is similar to FIG. 19, but with a different deployment mechanism.

The deployment mechanism 102 may be of other configurations for allowing the cutting element 4 to pivot between its cutting and retracted positions without departing from the scope of the present invention. For example, referring to FIGS. 23 and 24, another embodiment of the deployment mechanism is generally indicated at 102'. In this embodiment, the socket member 122 is replaced with a ramp member 130, and the cutting element does not include the ball member 120. The ramp member 130 has a proximal engagement face 132 that slopes distally generally toward the window 6. The angle of the sloped engagement face 132 may measure from about 20 degrees to about 45 degrees relative to the longitudinal axis LA of the catheter body 8. A distal face of the cutting element engages the engagement face 132 of the ramp member 130 when the drive shaft 20B is moved distally, such as by moving the lever 13 distally, so that the cutting element 4 pivots toward the window 6 and the cutting edge 22 extends through the window. Likewise, the cutting element 4 may be moved from its cutting position (FIG. 24) to its retracted position (FIG. 23) by moving the drive shaft 20B proximally, such as by moving the lever 13 proximally, such that the cutting element pivots away from the window as it disengages the sloped engagement face of the ramp member.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter comprising:
   an elongate catheter body configured for insertion into a body lumen of a subject, the catheter body having opposite distal and proximal ends, a longitudinal axis extending between the distal and proximal ends, and a window adjacent the distal end;
   a cutting element located generally at the distal end of the catheter body for rotation generally about the longitudinal axis of the catheter body, the cutting element having a proximal end portion, a distal end portion, and a longitudinal axis extending between the proximal and distal end portions;
   a rotatable drive shaft received in the catheter body and operatively connected to the cutting element for selectively imparting rotation to the cutting element relative to the catheter body about the longitudinal axis of the cutting element; and
   a deployment mechanism for selectively moving the cutting element between a retracted position, in which the cutting element does not extend through the window, and a cutting position, in which the cutting element extends at least partially through the window, the deployment mechanism including:
a socket member disposed in the catheter body, and a ball member extending distally from the cutting element and received in and operatively connected to the socket member, wherein the ball member is constrained axially relative to the socket member and is capable of pivoting relative to the socket member for allowing pivoting of the cutting element relative to the catheter body when the cutting element is moved from the retracted position to the cutting position, wherein the ball member is rotatable relative to the socket member about the longitudinal axis of the cutting element.

2. The tissue-removing catheter set forth in claim 1, wherein the ball member is fixedly connected to the cutting element, and wherein the socket member is longitudinally movable within the catheter body.

3. The tissue-removing catheter set forth in claim 2, wherein the deployment mechanism is configured such that proximal movement of the drive shaft relative to the catheter body causes the cutting element, the ball member, and the socket member to move proximally as an assembly relative to the catheter body to thereby impart pivoting of the cutting element relative to the socket to its cutting position, and distal movement of the driveshaft relative to the catheter body causes the cutting element, the ball member, and the socket member to move distally as an assembly relative to the catheter body to thereby impart pivoting of the cutting element relative to the socket to its retracted position.

4. The tissue-removing catheter set forth in claim 3, wherein the deployment mechanism further includes a ramp in the catheter body, wherein the cutting element is engageable with the ramp to impart pivoting of the cutting element relative to the socket member.

5. The tissue-removing catheter set forth in claim 4, wherein the deployment mechanism further includes a stop in the catheter body, wherein the stop is configured to engage the socket member and inhibit further proximal movement of the cutting element, the ball member, and the socket member when the cutting element is in the cutting position.

6. The tissue-removing catheter set forth in claim 4, wherein the rotatable drive shaft is connected to the proximal portion of the cutting element.

7. The tissue-removing catheter set forth in claim 3, wherein the cutting element includes an annular cutting edge at the proximal end portion of the cutting element for removing tissue from the wall of the body lumen.

8. The tissue-removing catheter set forth in claim 1, wherein the driveshaft includes an external thread.

9. The tissue-removing catheter set forth in claim 8, further comprising
a shearing member received in the catheter body adjacent to and proximal the cutting element, the shearing member defining a longitudinal bore through which the drive shaft extends, and a non-circular internal shearing edge associated with the bore and configured to interact with the external thread of the drive shaft when the drive shaft is rotated to shear removed tissue within the shearing member.

10. The tissue-removing catheter set forth in claim 9, wherein the shearing member has a longitudinal channel extending longitudinally through an interior surface defining the longitudinal bore to form the shearing edge.

11. The tissue-removing catheter set forth in claim 9, wherein the longitudinal bore has a generally oblong cross-sectional shape and the external thread has a generally circular cross-sectional shape, wherein the longitudinal bore is sized such that the external thread interacts with the shearing surface at two shearing regions as the drive shaft rotates.

12. The tissue-removing catheter set forth in claim 1, wherein the drive shaft is longitudinally moveable in the catheter body, wherein longitudinal movement of the drive shaft imparts movement of the cutting element between the retracted and cutting positions.

13. The tissue-removing catheter set forth in claim 1, wherein the cutting element has an annular cutting edge at the proximal end portion of the cutting element surrounding the longitudinal axis of the cutting element.

14. A method of removing tissue from a body lumen of a subject, the method comprising:
providing a tissue-removing catheter, the tissue-removing catheter including
an elongate catheter body configured for insertion into a body lumen of a subject, the catheter body having opposite distal and proximal ends, a longitudinal axis extending between the distal and proximal ends, and a window adjacent the distal end,
a cutting element located generally at the distal end of the catheter body for rotation generally about the longitudinal axis of the catheter body, the cutting element having a proximal end portion, a distal end portion, and a longitudinal axis extending between the proximal and distal end portions
a rotatable drive shaft received in the catheter body and operatively connected to the cutting element for selectively imparting rotation to the cutting element relative to the catheter body about the longitudinal axis of the cutting element, and
a deployment mechanism for selectively moving the cutting element between a between a retracted position, in which the cutting element does not extend through the window, and a cutting position, in which the cutting element extends at least partially through the window, the deployment mechanism including a socket member received in the catheter body, and a ball member extending distally from the distal end portion of the cutting element and received in and operatively connected to the socket member, wherein the ball member is constrained axially relative to the socket member and is capable of pivoting relative to the socket member for allowing pivoting of the cutting element relative to the socket member, wherein the ball member is rotatable relative to the socket member about the longitudinal axis of the cutting element;
inserting the catheter body into the body lumen, the cutting element being in the retracted position;
moving the cutting element, after said inserting, from the retracted position to the cutting position, whereby the ball member pivots relative to the socket member and the cutting element pivots relative to the socket.

15. The method set forth in claim 14, further comprising moving the socket member and the ball member concurrently with said moving the cutting element so that the socket member, the ball member, and the cutting element move as an assembly.

16. The method set forth in claim 15, further comprising rotating the drive shaft, after said moving the cutting element, to impart rotation to the cutting element and the ball member relative to the socket member about the longitudinal axis of the cutting element.

17. The method set forth in claim 16, further comprising moving the catheter body distally within the body lumen, after said rotating the drive shaft, to remove material from the body lumen.

18. The method set forth in claim 17, further comprising transporting the removed material proximally within the catheter body, concurrently with said moving the catheter body proximally and rotating the drive shaft, via an external thread on the rotating drive shaft.

19. The method set forth in claim 18, further comprising pinching the removed material between the external thread on the drive shaft and a shearing member in the catheter body, concurrently with said rotating the drive shaft.

\* \* \* \* \*